(12) United States Patent
Duggan

(10) Patent No.: US 10,035,775 B2
(45) Date of Patent: Jul. 31, 2018

(54) COMPOSITIONS FOR THE TREATMENT OF FIBROSIS AND FIBROSIS-RELATED CONDITIONS

(71) Applicant: VECTUS BIOSYSTEMS LIMITED, Rosebery (AU)

(72) Inventor: Karen Annette Duggan, Clovelly (AU)

(73) Assignee: VECTUS BIOSYSTEMS LIMITED, Rosebery (AU)

( * ) Notice: Subject to any disclaimer, the term of this patent is extended or adjusted under 35 U.S.C. 154(b) by 0 days.

(21) Appl. No.: 15/557,762

(22) PCT Filed: Mar. 18, 2016

(86) PCT No.: PCT/AU2016/000095
§ 371 (c)(1),
(2) Date: Sep. 12, 2017

(87) PCT Pub. No.: WO2016/145479
PCT Pub. Date: Sep. 22, 2016

(65) Prior Publication Data
US 2018/0072682 A1    Mar. 15, 2018

(30) Foreign Application Priority Data
Mar. 18, 2015 (AU) ............... 2015900979

(51) Int. Cl.
| C07D 233/78 | (2006.01) |
| C07C 39/12 | (2006.01) |
| C07C 59/54 | (2006.01) |
| C07C 215/54 | (2006.01) |
| C07C 239/20 | (2006.01) |
| C07D 207/26 | (2006.01) |
| C07D 207/38 | (2006.01) |
| C07D 209/48 | (2006.01) |
| C07D 233/96 | (2006.01) |
| C07D 261/14 | (2006.01) |
| C07D 263/38 | (2006.01) |
| C07D 263/44 | (2006.01) |

(52) U.S. Cl.
CPC ............ C07D 233/78 (2013.01); C07C 39/12 (2013.01); C07C 59/54 (2013.01); C07C 215/54 (2013.01); C07C 239/20 (2013.01); C07D 207/26 (2013.01); C07D 207/38 (2013.01); C07D 209/48 (2013.01); C07D 233/96 (2013.01); C07D 261/14 (2013.01); C07D 263/38 (2013.01); C07D 263/44 (2013.01)

(58) Field of Classification Search
CPC .. C07D 233/78; C07D 207/26; C07D 207/38; C07D 209/48; C07D 233/96; C07D 261/14; C07D 263/38; C07D 263/44; C07C 39/12; C07C 59/54; C07C 215/54; C07C 239/20
USPC ....................................... 514/376
See application file for complete search history.

(56) References Cited

U.S. PATENT DOCUMENTS

2011/0082109 A1    4/2011    Miyanaga

FOREIGN PATENT DOCUMENTS

| WO | 2015/039172 A1 | 3/2015 |
| WO | 2015/039173 A1 | 3/2015 |

OTHER PUBLICATIONS

Australian Patent Office; International Search Report of PCT/AU2016/000095; dated May 31, 2016; 4 pages.

*Primary Examiner* — Kristin A Vajda
(74) *Attorney, Agent, or Firm* — Kilpatrick Townsend & Stockton LLP

(57) ABSTRACT

The present invention relates to novel compounds and their use in the prophylactic and/or therapeutic treatment of fibrosis and fibrosis-related conditions.

21 Claims, 15 Drawing Sheets

COMPOSITIONS FOR THE TREATMENT OF FIBROSIS AND FIBROSIS-RELATED CONDITIONS

CROSS-REFERENCE TO RELATED APPLICATIONS

This application is a National Phase application under 35 USC § 371 of Application No. PCT/AU2016/000095, filed Mar. 18, 2016, which application claims priority to Australian Application No. 2015900979, filed Mar. 18, 2015, the teachings of which are hereby incorporated by reference in their entireties for all purposes.

FIELD OF THE INVENTION

The present invention relates to novel compounds and their use in the prophylactic and/or therapeutic treatment of fibrosis and fibrosis-related conditions.

The invention has been developed primarily for the treatment of fibrosis and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Repair of damaged tissues is a fundamental biological process. The repair process involves two distinct stages: a regenerative phase, in which injured cells are replaced by normal cells of the same type; and a phase known as fibrosis, in which connective tissue replaces normal parenchymal tissue. In most cases, both stages are required to slow or reverse the damage caused by a damaging agent. However, although initially beneficial, the healing process can become pathogenic if it continues unchecked, leading to considerable tissue remodelling and the formation of permanent scar tissue. Fibrotic scarring is often defined as a wound-healing response that has gone awry.

Fibrotic changes can occur in all the main tissues and organ systems, including the heart, kidney and liver, and the US government estimates that 45% of deaths in the US can be attributed to fibrotic disorders (Wynn, Nat Rev Immunol, 2004, 4(8):583-594). For example:
- fibrotic changes in the heart results in thickening of the heart valves and loss of flexibility in the cardiac muscle, which may lead to heart failure;
- fibrotic changes in the kidney may result in the destruction of renal tubules and interstitial capillaries, leading to progressive loss of renal function; and
- fatty liver disease (in which large vacuoles of triglyceride accumulate in liver cells) results in the accumulation of fibrosis in the liver, leading to in cirrhosis, liver failure and portal hypertension.

There is a need for agents that prevent or treat fibrosis and fibrosis-related conditions. In particular, there is a need for agents that prevent, reduce or slow the progression of fibrosis, reduce established fibrosis, prevent, reduce or slow renal tubular cell death, prevent, reduce or slow fat accumulation in the liver, and/or restore normal tissue architecture.

It is an object of the present invention to overcome or ameliorate at least one of the disadvantages of the prior art, or to provide a useful alternative.

SUMMARY OF THE INVENTION

According to one aspect, the present invention provides a compound of the formulae:

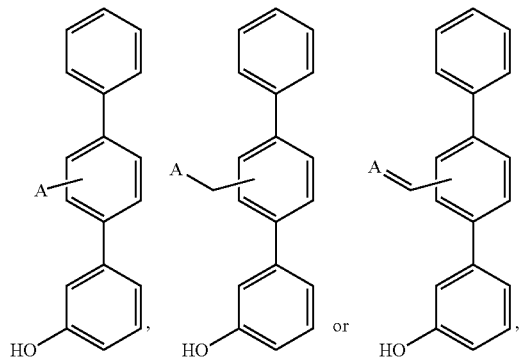

wherein:

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl, or a pharmacologically acceptable salt, stereoisomer diastereomer, enantiomer, racemate, hydrate and/or solvate thereof.

In one embodiment, the saturated, partly saturated or unsaturated 5- or 6-membered heterocyclyl contains one or more of N, S or O, optionally substituted with one or more oxo, $C_{1-6}$alkyl, amino, hydroxyl or halo substituents.

In one embodiment, the saturated, partly saturated or unsaturated 5- or 6-membered heterocyclyl is selected from pyrrolyl, pyrazolyl, imidazolyl, triazolyl, imidazolidinyl, pyrrolidinyl, pyrrolidinylidene, dihydropyrrolyl, isoxazolyl dihydrooxazolyl, isoxazolidinyl, oxazolidinyl and oxazolyl, optionally substituted with one or more oxo, $C_{1-6}$alkyl, amino, hydroxyl or halo substituents.

In one embodiment, the $C_{1-6}$alkoxyl amine is aminooxymethyl.

h one embodiment, the $C_{1-6}$alkyl amine is optionally substituted with one or more of $C_{1-6}$alkyl, $C_{1-6}$halo alkyl, hydroxyl or halo, preferably mono-, di- or tri-substituted halo alkyl, most preferably tri-fluoro methane.

In one embodiment, the $C_{0-6}$alkyl carboxylic acid is carboxylic acid.

In one embodiment, the $C_{1-6}$alkyl hydroxyl is methyl hydroxyl.

In one embodiment, the $C_{0-6}$alkyl bicyclic heterocyclyl is selected from indolyl, isoindolyl, insolinyl and isoindolinyl, optionally substituted with one or more oxo, preferably dioxo.

In one embodiment, the $C_{1-6}$alkoxyl bicyclic heterocyclyl is selected indolyl, isoindolyl, insolinyl and isoindolinyl, optionally substituted with one or more oxo, and wherein the $C_{1-6}$ alkoxyl is methoxy or ethoxy.

In one embodiment, A is selected from:
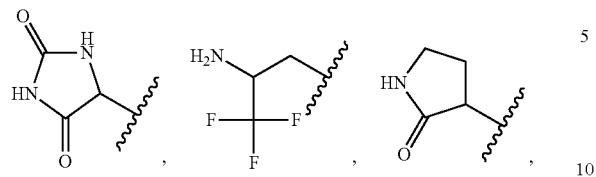
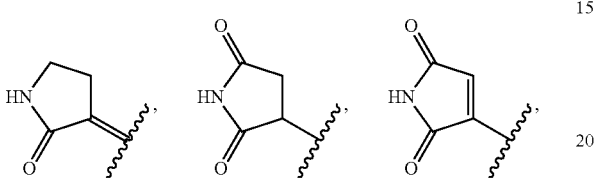
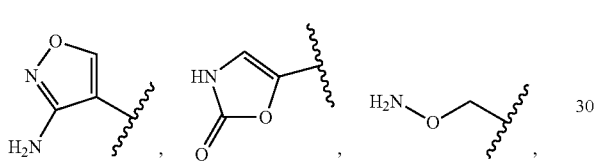
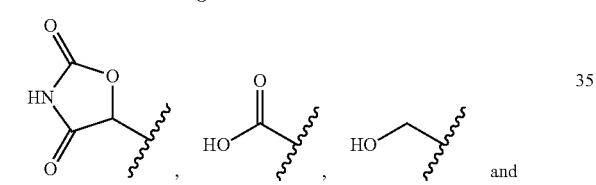
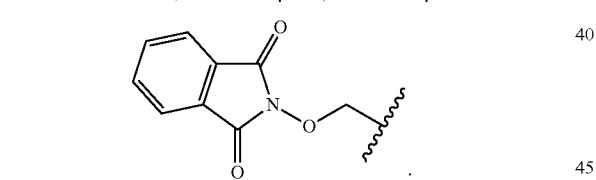 and
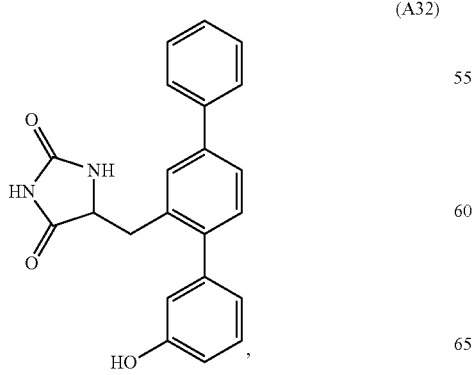
In one embodiment, the compound is selected from the group consisting of:
(A32)
(A6)
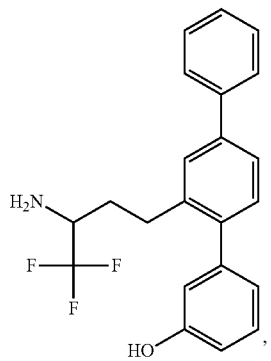
(A26)
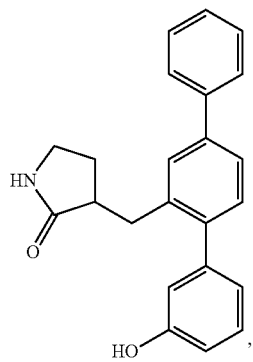
(A27)
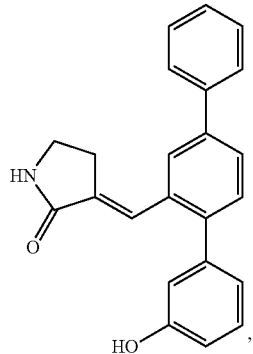
(A30)
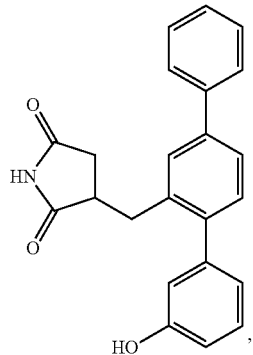

(A31)
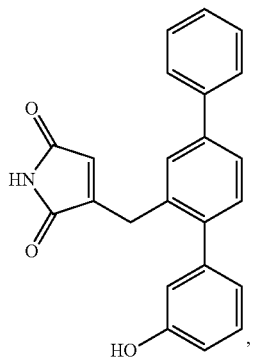
(A35)
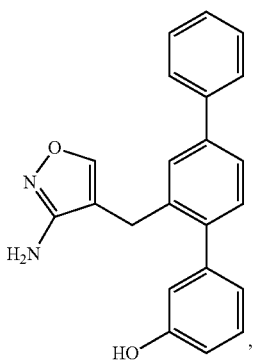
(A45)
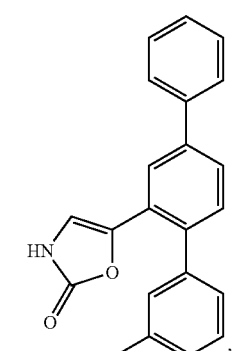
(A56)
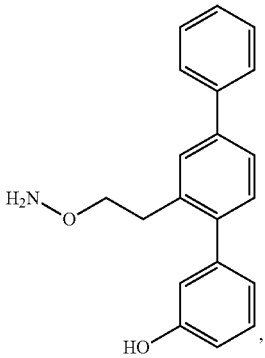
(A79)
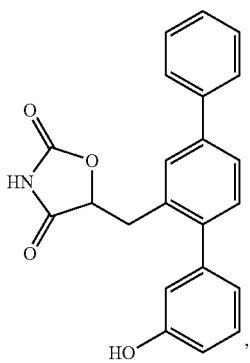
(A56k)
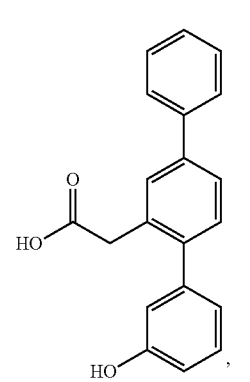
(A56f)
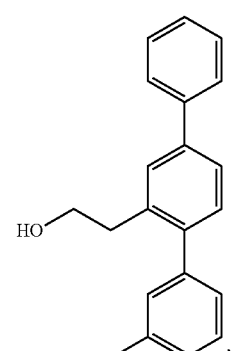
(A81)
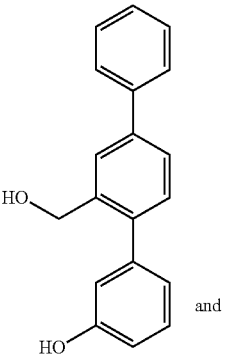
and -continued (A56g)

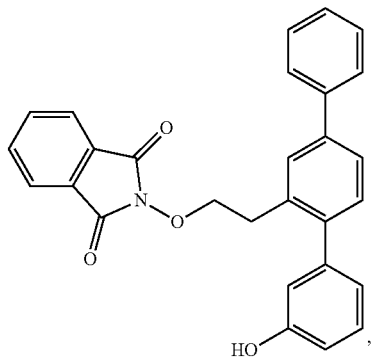

or a pharmacologically acceptable salt, stereoisomer, diastereomer, enantiomer, racemate, hydrate and/or solvate thereof.

According to another aspect, the present invention relates to a pharmaceutical composition comprising a compound of the present invention and a pharmaceutically acceptable excipient.

According to another aspect, the present invention relates to a method for the therapeutic treatment of fibrosis in a subject comprising administering to the subject a compound or a pharmaceutical composition according to the present invention.

According to another aspect, the present invention relates to a method for the prophylactic treatment of fibrosis in a subject comprising administering to the subject a compound or a pharmaceutical composition according to the present invention.

According to another aspect, the present invention relates to a compound or a pharmaceutical composition of the present invention for use in a method for the therapeutic treatment of fibrosis.

According to another aspect, the present invention relates to a compound or a pharmaceutical composition of the present invention for use in a method for the prophylactic treatment of fibrosis.

According to another aspect, the present invention relates to use of a compound of the present invention for the manufacture of a medicament for the therapeutic treatment of fibrosis.

According to another aspect, the present invention relates to use of a compound of the present invention for the manufacture of a medicament for the prophylactic treatment of fibrosis.

In one embodiment, the compound, pharmaceutical composition or medicament of the invention prevents, reduces or slows the progression of fibrosis.

In one embodiment, the compound, pharmaceutical composition or medicament of the invention reduces established fibrosis.

In one embodiment, the compound, pharmaceutical composition or medicament of the invention restores normal tissue architecture.

In one embodiment, the fibrosis is myocardial fibrosis.

In one embodiment, the fibrosis is kidney fibrosis.

In one embodiment, the fibrosis is liver fibrosis.

According to another aspect, the present invention relates to a method for preventing, reducing or slowing fat accumulation in the liver of a subject comprising administering to the subject a compound or a pharmaceutical composition according to the present invention.

According to another aspect, the present invention relates to a method for preventing, reducing or slowing renal tubular cell death in a subject comprising administering to the subject a compound or a pharmaceutical composition according to the present invention.

According to another aspect, the present invention relates to a method for restoring normal tissue architecture in a subject comprising administering to the subject a compound or a pharmaceutical composition according to the present invention.

According to another aspect, the present invention relates to a compound or a pharmaceutical composition of the present invention for use in a method for in preventing, reducing or slowing fat accumulation in the liver.

According to another aspect, the present invention relates to a compound or a pharmaceutical composition of the present invention for use in a method for preventing, reducing or slowing renal tubular cell death.

According to another aspect, the present invention relates to a compound or a pharmaceutical composition of the present invention for use in a method for restoring normal tissue architecture.

According to another aspect, the present invention relates to the use of a compound of the present invention for the manufacture of a medicament for preventing, reducing or slowing fat accumulation in the liver.

According to another aspect, the present invention relates to the use of a compound of the present invention for the manufacture of a medicament for preventing, reducing or slowing renal tubular cell death.

According to another aspect, the present invention relates to the use of a compound of the present invention for the manufacture of a medicament for restoring normal tissue architecture.

According to another aspect, the present invention relates to a compound of the formula:

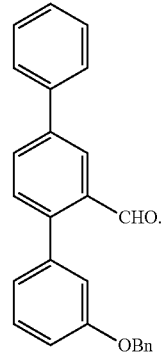 [SMILES: O=Cc1cc(-c2ccccc2)ccc1-c1cccc(OCc2ccccc2)c1]

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
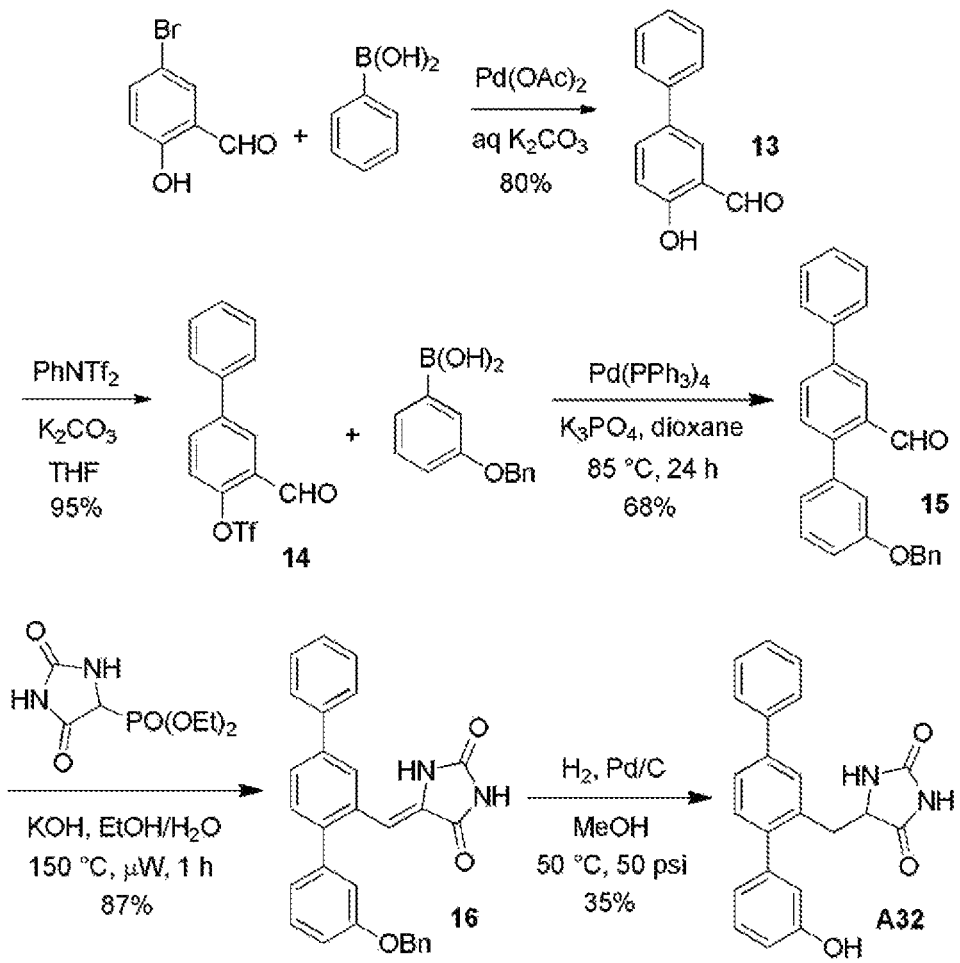
FIG. 1: Synthesis scheme for A32.

The present invention relates to compounds that show anti-fibrotic and related effects. The invention also relates to compounds that are effective in preventing, reducing or slowing the progression of fibrosis, reducing established fibrosis, preventing, reducing or slowing renal tubular cell death, preventing, reducing or slowing fat accumulation in the liver, and/or restoring normal tissue architecture.

The compounds of the present invention are represented by the formulae:

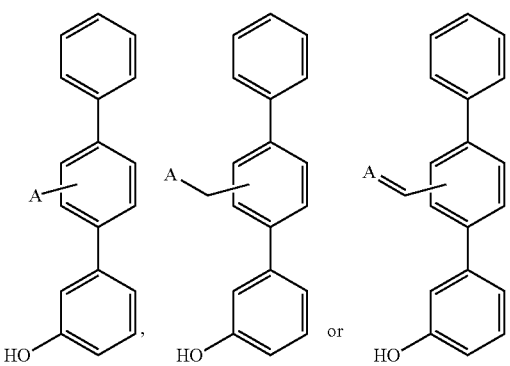

wherein:

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl, or a pharmacologically acceptable salt, stereoisomer, diastereomer, enantiomer, racemate, hydrate and/or solvate thereof.

The following compounds are specific, but non-limiting, examples of the compounds of the present invention:

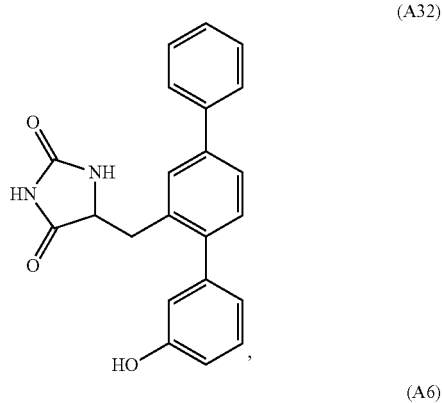

(A32)

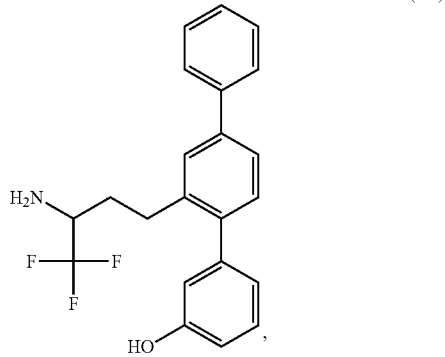

(A6)

(A26) 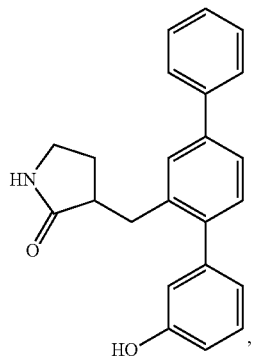
(A27) 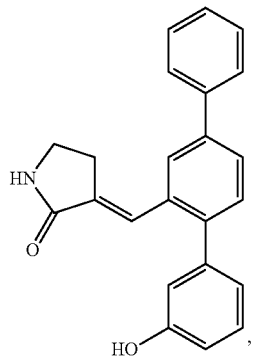
(A30) 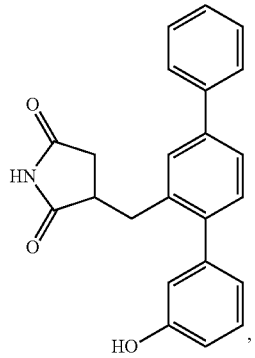
(A31) 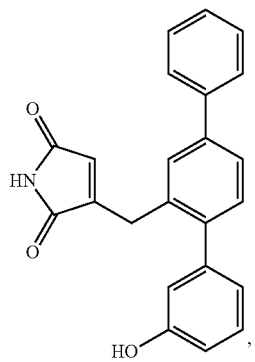
(A35) 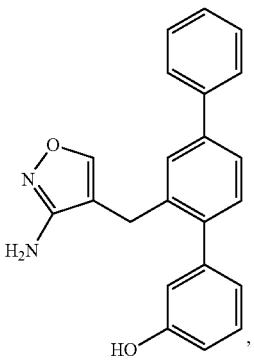
(A45) 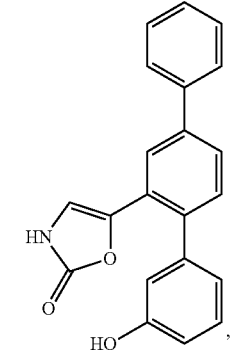
(A56) 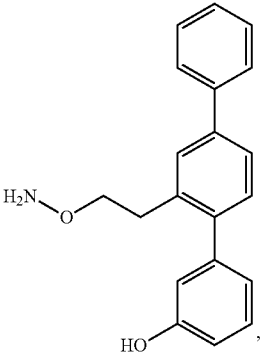
(A79) 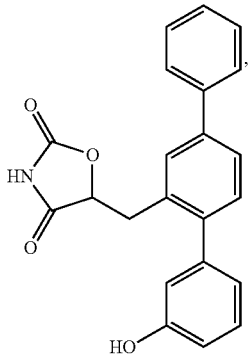

-continued

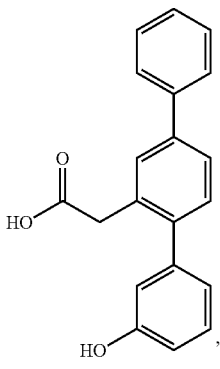

(A56k)

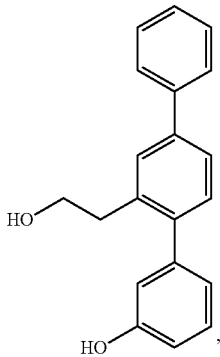

(A56f)

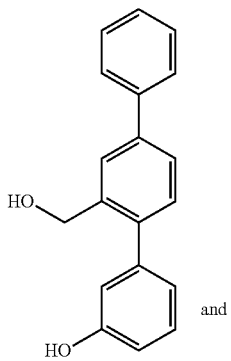

(A81)

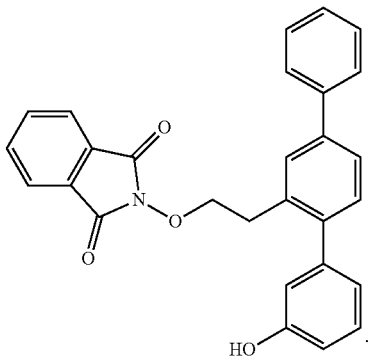

(A56g)

and

As used herein, the term "alkyl", alone or in combination, means a straight-chain or branched-chain alkyl radical of the formula —$C_nH_{(2n+1)}$. Examples of alkyls include methyl, ethyl, n-propyl, n-butyl, isobutyl, sec-butyl, tert-butyl, pentyl, isoamyl, hexyl, octyl and the like.

As used herein, the term "alkoxy", alone or in combination, means an alkyl bonded to an oxygen, wherein the term alkyl is as defined above. Examples of alkoxy include methoxy, ethoxy, n-propoxy, isopropoxy, n-butoxy, iso-butoxy, sec-butoxy, tart-butoxy and the like.

As used herein, the term "halo" designates —F, —Cl, —Br or —I.

As used herein, the term "hydroxy" designates —OH.

As used herein, the terms "amino" or "amine" designate —$NH_2$.

As used herein, the term "carboxylic acid" designates —C(O)OH.

As used herein, the term "oxy" designates —O—.

As used herein, the term "oxo" designates =O.

As used herein, the abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof, and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatisation with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

Other than where noted, compound synthesis methods are based on well established methods described in, for example March's Advanced Organic Chemistry: Reactions, Mechanisms, and Structure (2013) by Michael B. Smith; Advanced Organic Chemistry, Part A: Structure and Mechanisms (2008) and Advanced Organic Chemistry: Part B: Reaction and Synthesis (2010) by Francis A. Carey and Richard J. Sunberg; and Greene's Protective Groups in Organic Synthesis (2014) by Peter G. M. Wuts.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

The term "fibrosis" as used in the context of the present invention" refers to the formation of excess fibrous connective tissue in an organ or tissue, and includes myocardial fibrosis, kidney fibrosis and/or liver fibrosis.

All organs rely on specific, but different, arrangement of tissues (architecture) for normal function. Disease and/or fibrotic depositions can cause malfunction or poor function of the organ. Thus, restoring normal tissue architecture enables organs to regain their normal function.

In addition to treatment of established fibrosis, the compounds of the present invention may be used prophylactically in subjects at risk of developing fibrosis. As an example of subjects in the risk category for developing fibrosis are those having hypertension, diabetes, myocarditis, ischemic heart disease, Conn's Syndrome, pheochromocytoma, malignancies (such as myeloma and lymphoma) genetic predisposition (Alport syndrome, Wilsons disease, α1 anti-trypsin deficiency, haemachromatosis), infections (Hep B Hep C), high salt diet and/or receiving drugs used in cancer chemotherapy (such as daunorubicin, cisplatin, bleomycin), for treatment of hypomania (lithium), transplant rejection (cyclosporine, tacrolimus), arthritic conditions (NSAIDs, penicillamine, gold) and those exposed to heavy metals such as lead and cadmium. The term "prophylactic" as used in the context of the present invention is intended inter alia to encompass treatments used to prevent or slow down the development of fibrosis in the at risk group.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art, excipients include diluents, buffers, binders, lubricants, disintegrants, colorants, antioxidants/preservatives, pH-adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilising agent, a suspension aid, an emulsifying agent or a coating agent.

When the compound(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The dosage of a compound and frequency of administration that should be used can also be easily determined by the practicing physician in order to produce the desired response.

Although the dosage will vary depending on the symptoms, age and body weight of the patient, the nature and severity of the disorder to be treated or prevented, the route of administration and the form of the drug, in general, a daily dosage of from 0.0001 mg to 200 mg of the compound of the present invention may be a suitable effective amount for an adult human patient, and this may be administered in a single dose or in divided doses.

A "patient" or "subject" to be treated by the subject method can mean either a human or non-human subject.

An "effective amount" of a subject compound, with respect to a method of treatment, refers to an amount of the therapeutic in a preparation which, when applied as part of a desired dosage regimen provides a benefit according to clinically acceptable standards for the treatment or prophylaxis of a particular disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1: Synthesis of A32

The synthetic route used to prepare A32 is shown in FIG. 1. Briefly, 2-formyl aryl triflate 14 was prepared by means of a Suzuki cross-coupling reaction between 5-bromo-2-hydroxybenzaldehyde and phenylboronic acid to generate 2-hydroxy-5-phenyl benzaldehyde 13, which was subsequently reacted with N-phenyltriflamide. Another Suzuki reaction between 2-formyl aryl triflate 14 and 3-benzyloxyphenylboronic acid yielded terphenyl aldehyde 15, which underwent a Horner-Wadsworth-Emmons (HWE) reaction with diethyl 5-hydantoylphosphonate to form unsaturated hydantoin 16. In the presence of hydrogen and Pd/C, compound 16 underwent simultaneous olefin reduction and phenol deprotection to produce A32.

Production of 2-Hydroxy-5-phenylbenzaldehyde (13)

5-Bromosalicylaldehyde (2.49 g, 12.4 mmol), phenyl boronic acid (1.51 g, 12.4 mmol), palladium(II) acetate (14 mg, 0.5 mol %) and potassium carbonate (5.14 g, 37.2 mmol) were stirred in degassed water (75 mL) at ambient temperature for 2 h, under an argon atmosphere. The reaction was monitored by TLC (1:1 dichloromethane/pentane). Water (75 mL) was added and the reaction mixture acidified (pH 6) with 10% HCl, then extracted with ethyl acetate (3×). The combined organic extracts were washed with brine, then dried and concentrated. The crude material was passed through a short column of silica, eluting with 1:1 dichloromethane/pentane, then recrystallised from ethyl acetate/pentane to afford 2-hydroxy-5-phenylbenzaldehyde (1.89 g, 77%) as dark yellow crystals (can be triturated with pentane instead recrystallised if desired); mp 100-101° C.

$^1$H NMR (400 MHz, CDCl$_3$) δ 10.99 (s, 1H); 9.97 (s, 1H); 7.78-7.73 (m, 2H); 7.56-7.52 (m, 2H); 7.47-7.41 (m, 2H); 7.37-7.32 (m, 1H); 7.09-7.04 (m, 1H). $^{13}$C NMR (100 MHz, CDCl$_3$) δ 196.9, 161.2, 139.6, 136.0, 133.6, 132.1, 129.2, 127.6, 126.8, 121.0, 118.4. EIMS: m/z 198 [M]$^+$. HRMS calcd for C$_{13}$H$_{10}$O$_2$ 198.0675, found 198.0677.

Production of 3-formylbiphenyl-4-yl trifluoromethanesulfonate (14)

2-Hydroxy-5-phenylbenzaldehyde (100 mg, 0.50 mmol), N-phenyltriflamide (180.0 mg, 0.51 mmol) and potassium carbonate (209 mg, 1.51 mmol) were stirred in dry THF in a sealed tube, and heated at 120° C. for 6 min, using microwave irradiation. The solvent was removed under reduced pressure; water and dichloromethane were added and the layers separated. The aqueous layer was extracted further with dichloromethane (2×). The combined organic extracts were washed with brine (1×), then dried and concentrated. Purified by radial chromatography, eluting with 1:1 dichloromethane/pentane, to afford 3-formylbiphenyl-4-yl-trifluoromethanesulfonate (143 mg, 86%) as a clear, colourless oil. $^1$H NMR (200 MHz, CDCl$_3$) δ 10.32 (s, 1H); 8.17 (d, 1H, J=2.4 Hz); 7.89 (dd, 1H, J=8.6, 2.5 Hz); 7.63-7.36 (m, 6H). $^{13}$C NMR (125 MHz, CDCL$_3$) δ 186.5, 149.1, 142.3, 138.0, 134.1, 129.2, 129.1, 128.8, 128.6, 127.2, 122.9, 118.7 (q, J$_{CF}$=320.9 Hz). $^{19}$F NMR (188 MHz, CDCl$^3$) δ-73.2. EIMS: m/z 330 [M]$^+$. HRMS calcd for C$_{14}$H$_9$F$_3$O$_2$S, 330.0168, found 330.0163.

Production of 2'[3-benzyloxy-(1,1':4',1"-terphenyl)] carbaldehyde (15)

3-Formylbiphenyl-4-yl trifluoromethanesulfonate (153 mg, 0.463 mmol), 3-benzyloxyphenylboronic acid (116 mg, 0.51 mmol), tetrakis(triphenylphosphine)palladium(0) (13 mg, 2.5 mol %) and anhydrous potassium phosphate (147 mg, 0.695 mmol) were placed in a Schlenk flask, under an argon atmosphere. Degassed 1,4-dioxane (2 mL) was added and the mixture purged with argon. The reaction mixture was heated at 85° C. until complete conversion was observed (monitored by GCMS); generally required overnight reaction time. The reaction mixture was diluted with benzene (4 mL) and treated with 30% aqueous hydrogen peroxide (10 mL). The product was extracted with diethyl ether (3×); the combined organic extracts were washed with brine then dried and concentrated. Purified by radial chromatography, eluting with 1:1 dichloromethane/pentane, to afford 2'-[3-benzyloxy-(1,1':4',1"-terphenyl)]carbaldehyde (122 mg, 72%) as a clear, colourless, viscous oil. $^1$H NMR (400 MHz, CDCl$_3$) δ 10.02 (s, 1H); 8.24 (dd, 1H, J=2.1, 0.3 Hz); 7.86 (dd, 1H, J=8.0, 2.1 Hz); 7.68-7.64 (m, 2H); 7.56-7.30 (m, 10H); 7.08-7.02 (m, 2H); 7.01-6.97 (m, 1H); 5.11 (s, 2H). $^{13}$C NMR (100 MHz, CCl$_3$) δ 192.6, 159.0, 144.8, 141.0, 139.7, 139.1, 136.9, 134.2, 132.2, 131.4, 129.8, 129.2, 128.9, 128.4, 128.2, 127.8, 127.3, 126.1, 123.2, 116.9, 114.9, 70.4. EIMS: m/z 364 [M]$^+$. HRMS calcd for C$_{26}$H$_{20}$O$_2$ 364.1458, found 364.1450.

Production of (E/Z)-5-((3-(Benzyloxy)-[1,1':4',1"-terphenyl]-2'-yl)methylene) imidazolidine-2,4-dione (16)

2'[3-Benzyloxy-(1,1':4',1"-terphenyl)]carbaldehyde (15) (978 mg, 2.7 mmol), diethyl 5-hydantoylphosphonate (949 mg, 4.0 mmol), powdered potassium hydroxide (301 mg, 5.4 mmol), ethanol (20 mL) and water (0.5 mL) were combined in a 20 mL reaction vial and heated at 150° C. for 1 h using microwave irradiation (300 watt). The mixture was poured into water and the solid collected by filtration using Whatman's 542 hardened ashless filter paper, washing thoroughly with water. The solid was taken up in hot ethanol and again poured slowly into water with stirring to produce a fine precipitate. The solid was collected by filtration (Whatman's 542 hardened ashless filter paper), washed thoroughly with water then dried in vacuo at 40° C. to afford (E/Z)-5-((3-(benzyloxy)-[1,1':4',1"-terphenyl]-2'-yl)methylene)imidazolidine-2,4-dione (16) (1.04 g, 87%) as a pale yellow solid. Further purification was not required. $^1$H NMR (200 MHz, DMSO-d$_6$) δ 10.99 (br s, 2H); 7.90-7.21 (m, 14H), 7.17-6.89 (m, 3H), 6.21 (s, 1H), 5.14 (s, 2H). $^{13}$C NMR (50 MHz, DMSO-d$_6$) δ 165.5, 158.3, 155.9, 141.0, 140.5, 139.8, 139.6, 137.0, 131.2, 130.5, 129.5, 129.2, 128.8, 128.4, 127.8, 127.6 (two signals coincident), 127.1, 126.9, 122.1, 115.9, 114.2, 106.8, 69.4 (one signal not observed). EIMS: m/z Found: M$^{+•}$ 446.1619, C$_{29}$H$_{22}$N$_2$O$_3$ requires 446.1625. EIMS: m/z 446 (M$^{+•}$, 8%), 383 (5), 356 (15), 355 (57), 313 (10), 312 (42), 284 (13), 258 (6), 257 (24), 228 (6), 92 (8), 91 (100).

Production of 5-((3-Hydroxy-[1,1':4',1"-terphenyl]-2'-yl)methyl)imidazolidine-2,4-dione (A32)

(E/Z)-5-((3-(Benzyloxy)-[1,1':4',1"-terphenyl]-2'-yl) methylene)imidazolidine-2,4-dione (16) (1.02 g, 2.3 mmol) and 10% palladium on carbon (50% wt in H$_2$O, 200 mg) in methanol (50 mL) were stirred at rt under a hydrogen atmosphere at 50 psi for 1 h. The methanol was removed and the residue taken up in DCM and gravity filtered through GF paper. Purified by radial chromatography (3:97 methanol: DCM→5:95 methanol:DCM) and preparative HPLC (compound pre-adsorbed onto Chromatorex C$_{18}$ silica, 45% ACN/H$_2$O, 80 mL/min, 240 nm, 300×40 mm Deltaprep C$_{18}$ column) to afford 5-((3-hydroxy-[1,1':4',1"-terphenyl]-2'-yl) methyl)imidazolidine-2,4-dione (A32) (285 mg, 35%) as a fine white powder; mp 214-216° C. $^1$H NMR (200 MHz, DMSO-d$_6$) δ 10.59 (br s, 1H), 9.54 (br s, 1H), 7.90 (m, 1H), 7.80-7.31 (m, 7H), 7.30-7.15 (m, 2H), 6.84-6.67 (m, 3H), 4.22 (m, 1H), 3.12 (dd, 1H, J 4.5, 14.6 Hz), 2.81 (dd, 1H, J 9.0, 14.6 Hz). $^{13}$C NMR (50 MHz, DMSO-d$_6$) δ 175.4, 157.3, 157.1, 141.8, 141.3, 139.9, 139.1, 134.4. 130.3, 129.2, 128.8, 128.0, 127.4, 126.8, 124.8, 119.8, 116.0, 114.1, 57.9, 34.8. EIMS: m/z Found: M$^{+•}$ 358.1306, C$_{22}$H$_{18}$N$_2$O$_3$ requires 358.1312. EIMS: m/z 358 (M$^{+•}$, 50%), 260 (23), 259 (100). HPLC purity (40% ACN/H$_2$O, 263 nm): 99.26%.

Example 2: Synthesis of A6

Figure 2:
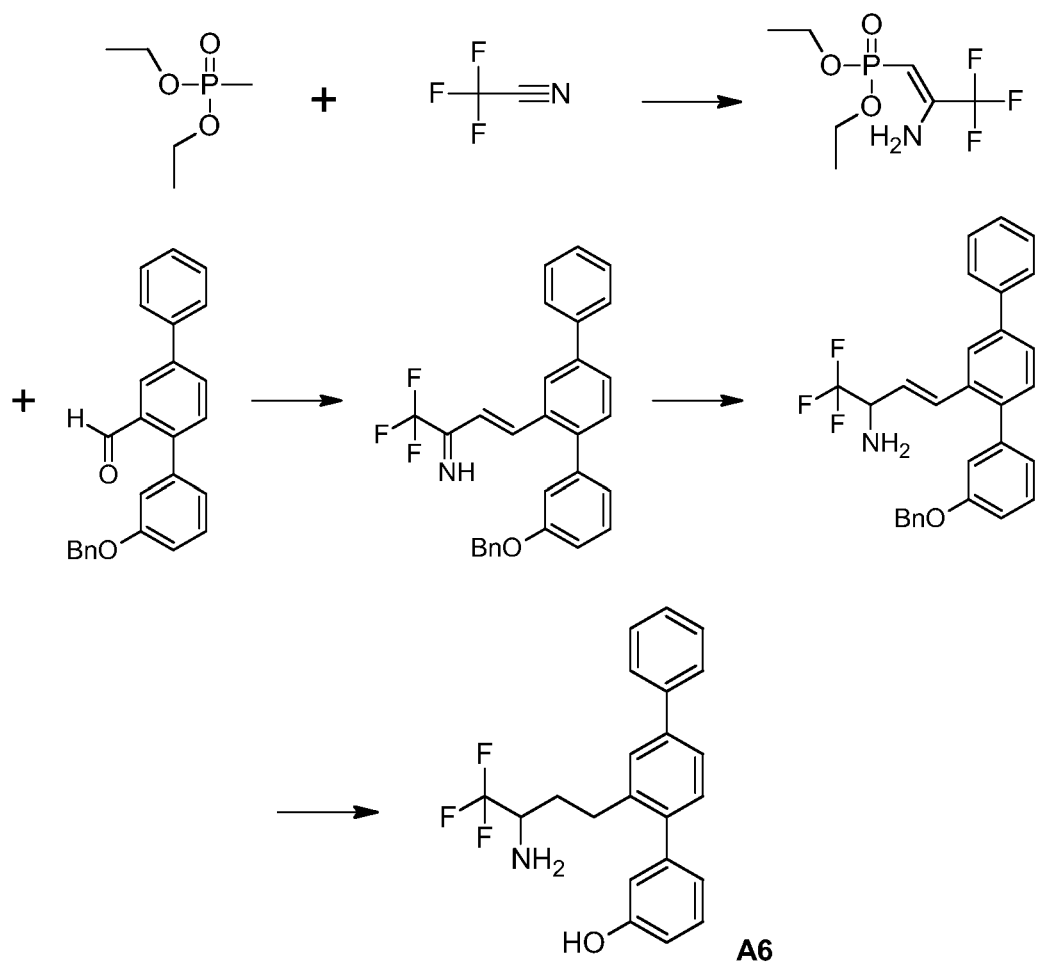
FIG. 2: Synthesis scheme for A6.

The synthetic route used to prepare A6 is shown in FIG. 2.

Production of Diethyl [2-amino-3,3,3-trifluoroprop-1-en-1-yl]phosphonate

A solution of diethyl methylphosphonate (1.000 g, 6.57 mmol) in anhyd. tetrahydrofuran (33 mL) was prepared under nitrogen and cooled in a −80° C. cooling bath. Methyllithium solution, 1.21 M in diethyl ether (5.5 mL, 6.6 mmol) was added dropwise. The mixture was stirred at −80° C. under nitrogen for 1 h.

Trifluoroacetic acid (0.71 mL, 9.6 mmol) was added dropwise to anhyd. pyridine (11.7 mL, 145 mmol) under nitrogen. The cloudy vapours were cleared under a stream of nitrogen. A 50 mL round bottomed flask was charged with trifluoroacetamide (3.177 g, 33.4 mmol) and dissolved in the pyridine/trifluoroacetic acid mixture under nitrogen. A cannula was inserted into the head space above this solution while the other end of the cannula was inserted into the phosphonate solution. Trimethylacetyl chloride (7.3 mL, 59.3 mmol) was added dropwise to the trifluoroacetamide solution over a 80 min period. The phosphonate solution was stirred at −80° C. during the addition, then for a further 4 h before being allowed to warm to room temperature overnight.

The reaction mixture was partitioned between dichloromethane (20 mL) and water (60 mL). The phases were separated. The aqueous layer was extracted with dichloromethane (10 mL). The combined dichloromethane layers were washed with brine (20 mL), dried over anhyd. sodium sulfate and filtered. The filtrate was evaporated to dryness. The residue was purified by flash chromatography (ethyl acetate/hexanes) to give the title compound as a pale yellow powder (638 mg, 39%). $^1$H NMR (400 MHz, CDCl$_3$) 5.71 (br. s, 2H), 4.46 (d, J=8.6 Hz, 1H), 3.98-4.15 (m, 4H), 1.34 (t, J=7.0 Hz, 6H). [Reference: F. Palacios et al., *J. Org. Chem.* 2004, 69, 8767-8774].

Production of 1,1,1-Trifluoro-4-[3-(benzyloxy)-1,1': 4',1''-terphenyl-2'-yl]but-3-en-2-amine Solutions of diethyl [2-amino-3,3,3-trifluoroprop-1-en-1-yl]phosphonate (638 mg, 2.58 mmol) in anhyd. tetrahydrofuran (7.7 mL) and 3-(benzyloxy)-1,1':4',1''-terphenyl-2'-carbaldehyde (944 mg, 2.59 mmol) in anhyd. tetrahydrofuran (7.7 mL) were prepared under nitrogen. The phosphonate solution was cooled to −5° C. Butyllithium solution, 1.47 M in hexanes (1.8 mL, 2.65 mmol) was added dropwise. The mixture was stirred at −5° C. under nitrogen for 1 h. The aldehyde solution was added dropwise via syringe. The mixture was stirred under nitrogen at −5° C. for 15 min, then at room temperature for 70 min.

The reaction mixture was cooled to −78° C. Sodium borohydride (196 mg, 5.18 mmol) was added, followed by the dropwise addition of methanol (15 mL). The mixture was stirred at −78° C. for 80 min, then allowed to warm to room temperature overnight.

Hydrochloric acid (1M, 5 mL) was added cautiously. The mixture was stirred at room temperature for 45 min, adjusted to pH 11 (universal indicator) by the addition of sodium hydroxide (253 mg, 6.33 mmol) and extracted with ethyl acetate (30 mL). The aqueous layer was partitioned between ethyl acetate (10 mL) and water (10 mL), and the phases separated. The combined ethyl acetate layers were washed with brine (2×20 mL), dried over anhyd. sodium sulfate and filtered. The filtrate was evaporated to dryness. The residue was purified by flash chromatography (dichloromethane) to give a mixture of the title compound (72 mol %) and the benzyl alcohol from reduction of the starting aldehyde (28 mol %) (467 mg, 39%). $^1$H NMR (400 MHz, CDCl$_3$; selected resonances) Title compound C(3)H: 6.14 (dd, J=15.8, 6.8 Hz, 1H), Benzyl alcohol ArCH$_2$OH: 4.65 (d, J=5.7 Hz, 2H).

Production of 2'-(3-Amino-4,4,4-trifluorobutyl)-1,1': 4',1''-terphenyl-3-ol (A6)

A solution of crude 1,1,1-trifluoro-4-[3-(benzyloxy)-1,1: 4',1''-terphenyl-2'-yl]but-3-en-2-amine (576 mg, 1.25 mmol) in acetic acid (20 mL) was added to 10% palladium on carbon (131 mg, 0.12 mmol wrt Pd). The mixture was hydrogenated at 2.1 bar for 18 h. The mixture was filtered through celite. The filter cake was washed with acetic acid (2×20 mL). The combined filtrates were evaporated to dryness. The residue was partitioned between ethyl acetate (20 mL) and sat. sodium hydrogen carbonate solution (20 mL). The ethyl acetate layer was washed with sat. sodium hydrogen carbonate solution (20 mL) and brine (20 mL), dried over anhyd. sodium sulfate, and filtered. The filtrate was evaporated to dryness. The residue was purified by flash chromatography (ethyl acetate/hexanes) to give the title compound as a pale orange brown oil which solidified on standing (323 mg, 69%). The product was suspended in 7.5% dichloromethane/hexanes and isolated by filtration to give an off-white powder. $^1$H NMR (400 MHz, CDCl$_3$) 7.58-7.67 (m, 2H), 7.42-7.55 (m, 4H), 7.33-7.40 (m, 1H), 7.27-7.33 (m, 2H), 6.88-6.95 (m, 1H), 6.79-6.87 (m, 2H), 5.26 (br. s, 1H), 2.93-3.08 (m, 2H), 2.69-2.82 (m, 1H), 1.85-1.98 (m, 1H), 1.48-1.61 (m, 1H), 1.17 (br. s, 2H); HPLC (water/ACN+0.1% TFA gradient) 99.40% at 220 nm; LCMS [M+H]$^+$=372.2.

Example 3: Synthesis of A30

Figure 3:
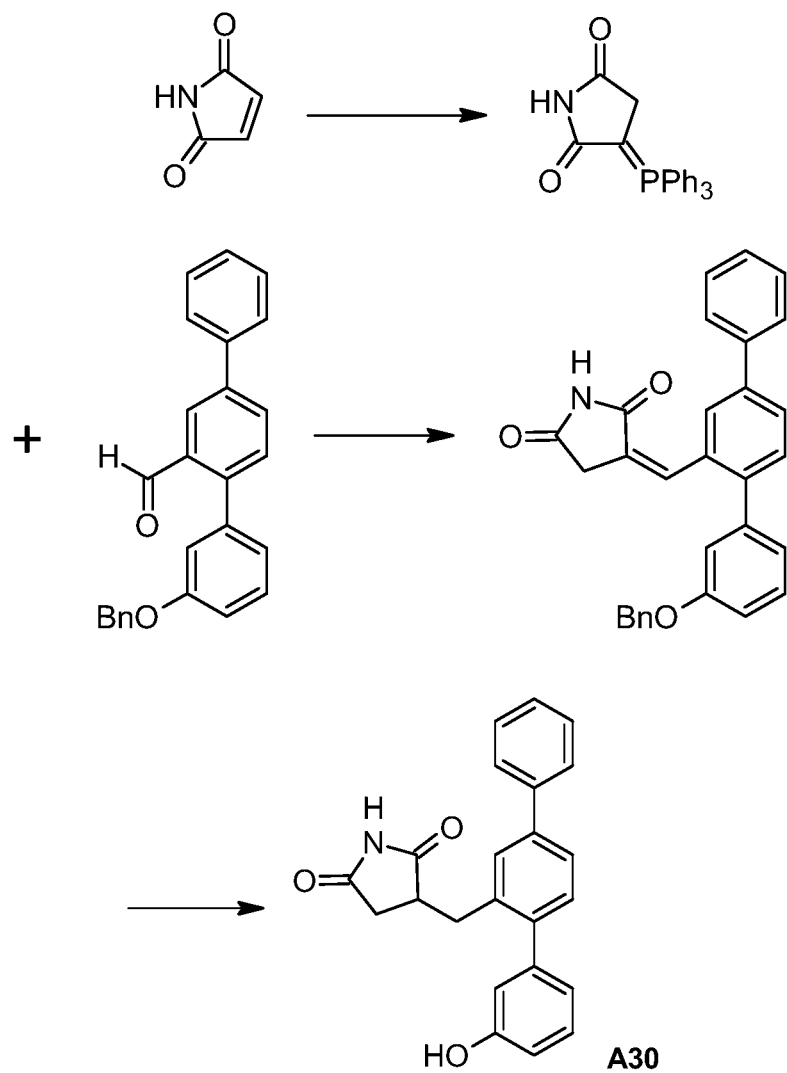
FIG. 3: Synthesis scheme for A30.

The synthetic route used to prepare A30 is shown in FIG. 3.

Production of 3-(Triphenyl-l$^5$-phosphanylidine)pyrrolidine-2,5-dione

A suspension of maleimide (3.17 g, 32.7 mmol) and triphenylphosphine (8.56 g, 32.6 mmol) in acetone (165 mL) was heated at reflux under nitrogen for 1 h. The reaction mixture was cooled to room temperature and filtered. The filter cake was washed with acetone (3×20 mL) and dried under vacuum to give the title compound as a white powder (7.21 g, 61%). $^1$H NMR (400 MHz, DMSO-d$_6$) 9.73 (br. s, 1H), 7.66-7.75 (m, 3H), 7.53-7.65 (m, 12H), 2.89 (s, 2H).

The filtrates from above were combined and concentrated to remove ca. 120 mL of solvent. The remaining material was heated at reflux under nitrogen for 2 h, allowed to cool to room temperature and filtered. The filter cake was washed with acetone (3×10 mL) and dried under vacuum to give a further crop of the title compound as a white powder (2.63 g, 22%). [Reference: G. Brackman et al., *Bioorg. Med. Chem.* 2013, 21, 660-667].

Production of 3-{[3-(Benzyloxy)-1,1':4',1''-terphenyl-2'-yl]methylidene}pyrrolidine-2,5-dione A mixture of 3-(benzyloxy)-1,1':4',1''-terphenyl-2'-carbaldehyde (1.71 g, 4.69 mmol) and 3-(triphenyl-l$^5$-phosphanylidine)pyrrolidine-2,5-dione (1.69 g, 4.69 mmol) in methanol (15 mL) was heated at reflux under nitrogen for 1.5 h. The reaction mixture was filtered hot. The filter cake washed with methanol (2×25 mL) and air dried to give the title compound as a yellow powder (1.05 g, 50%). $^1$H NMR (400 MHz, CDCl$_3$) 8.18 (s, 1H), 7.67-7.69 (m, 3H), 7.61 (d, J=8.0 Hz, 2H), 7.33-7.51 (m, 10H), 7.02 (dd, J=8.0, 2.0 Hz, 1H), 6.95 (s, 1H), 6.92 (d, J=7.6 Hz, 1H), 5.10 (s, 2H), 3.56 (s, 2H); LCMS [M+H]$^+$=446.3, [M+Na]$^+$=468.2, [M−H]$^-$=444.2.

Production of 3-[(3-Hydroxy-1,1':4',1''-terphenyl-2'-yl)methyl]pyrrolidine-2,5-dione (A30)

A mixture of 3-{[3-(benzyloxy)-1,1':4',1''-terphenyl-2'-yl]methylidene}pyrrolidine-2,5-dione (2.25 g, 5.05 mmol), ethyl acetate (200 mL) and triethylamine (40 drops) was degassed by bubbling nitrogen (2 L) through the mixture over a 5-10 min period. 10% Palladium on carbon (0.23 g) was added under nitrogen. The mixture was hydrogenated at atmospheric pressure at reflux overnight. The hot reaction mixture was filtered through celite and the filter cake washed with ethyl acetate (3×50 mL). The combined filtrates were evaporated to dryness. The residue was purified by flash chromatography (ethyl acetate/hexanes). The product was concentrated from ethanol (100 mL) and dried under high vacuum for 3 days to give the title compound as a colourless glass (1.61 g, 89%). $^1$H NMR (400 MHz, CDCl$_3$) 7.89 (br. s, 1H), 7.61 (d, J=6.8 Hz, 2H), 7.53 (dd, J=8.0, 2.0 Hz, 1H), 7.44-7.48 (m, 3H), 7.37 (t, J=7.2 Hz, 1H), 7.31 (t, J=7.2 Hz, 2H), 6.81-6.90 (m, 3H), 5.40 (br. s, 1H), 3.51 (dd, J=14.0, 4.8 Hz, 1H), 3.01 (m, 1H), 2.87 (dd, J=14.0, 10.4 Hz, 1H), 2.56 (dd, J=18.4, 9.2 Hz, 1H), 2.25 (dd, J=18.4, 5.6 Hz, 1H); HPLC 99.01% at 220 nm; LCMS [M+H]$^+$=358.2, [M+Na]$^+$=380.1, [M−H]$^−$=356.2.

Example 4: Synthesis of A56f, A56q and A56

Figure 4:
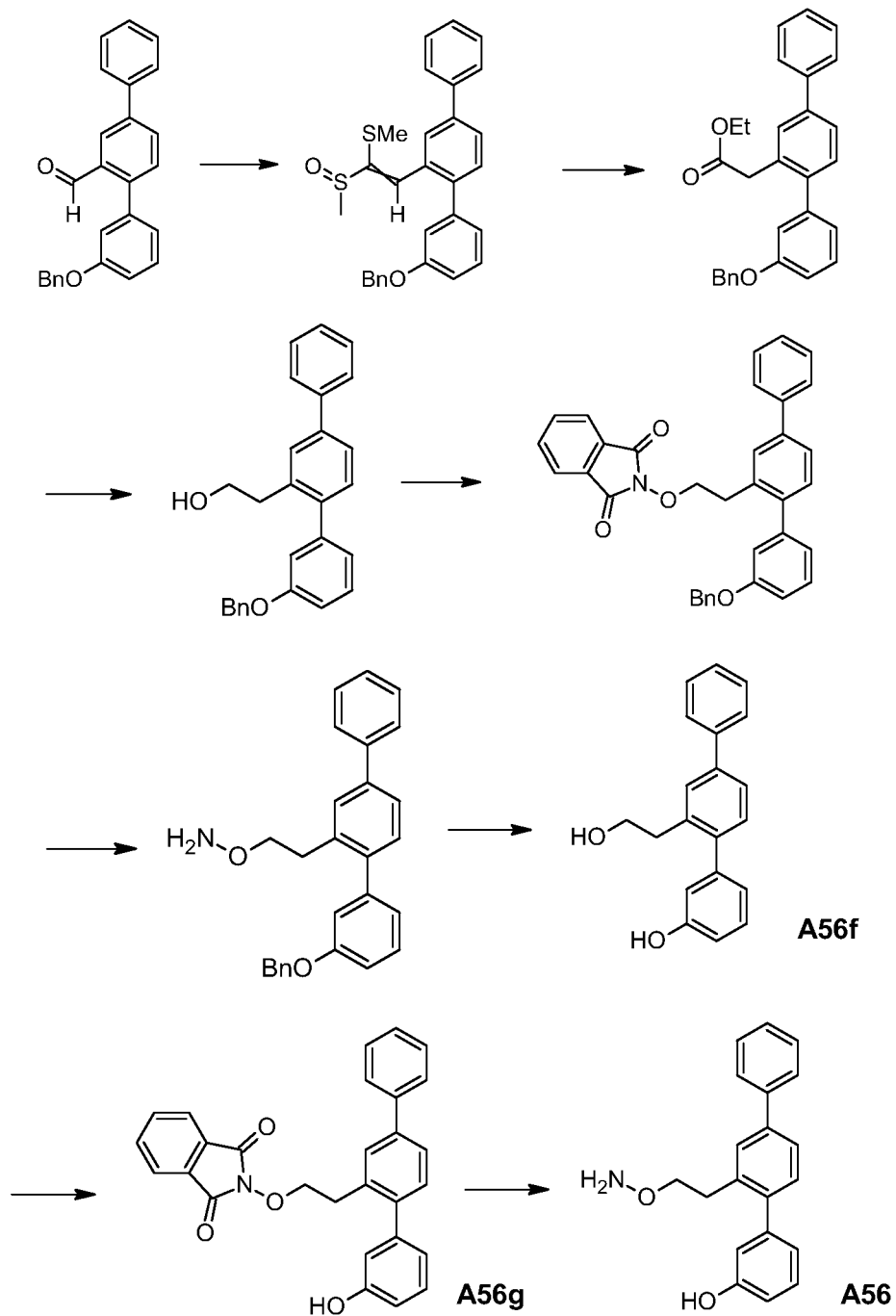
FIG. 4: Synthesis scheme for A56f, A56g and A56.

The synthetic route used to prepare of A56f, A56g and A56 is shown in FIG. 4.

Production of 2-[3-(Benzyloxy)-1,1':4',1"-terphenyl-2'-yl]-1-(methylsulfanyl)ethenyl methyl sulfoxide 3-(Benzyloxy)-1,1':4',1"-terphenyl-2'-carbaldehyde (5.330 g, 14.6 mmol) was dissolved in tetrahydrofuran (65 mL). Methyl (methylsulfinyl)methyl sulfide (2.745 g, 22.1 mmol) and sodium hydroxide (654 mg, 16.4 mmol) were added. The mixture was heated at reflux under nitrogen overnight. The reaction mixture was partitioned between ethyl acetate (400 mL) and water (200 mL). The aqueous layer was extracted with ethyl acetate (2×200 mL). The combined ethyl acetate layers were washed with water (2×200 mL) and brine (200 mL), dried over anhyd. sodium sulfate, and filtered. The filtrate was evaporated to dryness. The residue was purified by flash chromatography (ethyl acetate/dichloromethane) to give the title compound as a pale orange oil (3.733 g, 54%). $^1$H NMR (400 MHz, CDCl$_3$) 8.14 (d, J=1.4 Hz, 1H), 7.62-7.72 (m, 4H), 7.42-7.53 (m, 5H), 7.39 (t, J=7.3 Hz, 3H), 7.29-7.36 (m, 2H), 6.90-7.01 (m, 3H), 5.10 (s, 2H), 2.70 (s, 3H), 2.28 (s, 3H).

Production of Ethyl [3-(benzyloxy)-1,1':4',1"-terphenyl-2'-yl]acetate

2-[3-(Benzyloxy)-1,1':4',1"-terphenyl-2'-yl]-1-(methylsulfanyl)ethenyl methyl sulfoxide (3.733 g, 7.93 mmol) was dissolved in ethanol (70 mL). Conc. hydrochloric acid (6.6 mL) was added and the mixture heated at reflux for 5 days. The reaction mixture was partitioned between ethyl acetate (500 mL) and water (250 mL). The ethyl acetate layer was washed with water (200 mL) and brine (200 mL), dried over anhyd. sodium sulfate, and filtered. The filtrate was evaporated to dryness. The residue was purified by flash chromatography (dichloromethane) to give the title compound as a yellow-orange oil (2.129 g, 64%). $^1$H NMR (400 MHz, CDCl$_3$) 7.60-7.68 (m, 2H), 7.59 (br. s, 1H), 7.55 (dd, J=8.0, 1.6 Hz, 1H), 7.42-7.50 (m, 4H), 7.29-7.42 (m, 6H), 6.92-7.04 (m, 3H), 5.09 (s, 2H), 4.10 (q, J=7.0 Hz, 2H), 3.65 (s, 2H), 1.21 (t, J=7.1 Hz, 3H); LCMS [M+H]$^+$=423.1.

Production of 2-[3-(Benzyloxy)-1,1':4',1"-terphenyl-2'-yl]ethanol

Ethyl [3-(benzyloxy)-1,1':4',1"-terphenyl-2'-yl]acetate (2.129 g, 5.04 mmol) was dissolved in anhyd. tetrahydrofuran (20 mL) under nitrogen. A suspension of lithium aluminium hydride (306 mg, 8.06 mmol) in anhyd. tetrahydrofuran (10 mL) was prepared under nitrogen and cooled in an ice/water bath. The ester solution was added drop wise to the lithium aluminium hydride suspension. The mixture was stirred at room temperature under nitrogen overnight. The reaction mixture was cooled in an ice/water bath. The excess lithium aluminium hydride was quenched by the drop wise addition of water (0.37 mL), 15% sodium hydroxide solution (0.37 mL) and water (1.5 mL). The mixture was stirred for 30 min. Ethyl acetate (60 mL) was added and the mixture filtered through celite. The filter cake was washed with ethyl acetate (2×30 mL). The combined filtrates were evaporated to dryness to give the title compound as a pale orange oil (2.046 g, 107%). $^1$H NMR (400 MHz, CDCl$_3$) 7.59-7.67 (m, 2H), 7.55 (d, J=1.6 Hz, 1H), 7.50 (dd, J=7.9, 1.9 Hz, 1H), 7.43-7.48 (m, 4H), 7.28-7.42 (m, 6H), 6.92-7.03 (m, 3H), 5.11 (s, 2H), 3.66-3.74 (m, 2H), 2.92 (t, J=6.8 Hz, 2H), 1.21 (t, J=5.9 Hz, 1H); LCMS [M+H−H$_2$O]$^+$=363.3, [2M+H]$^+$=761.6.

Production of 2-{2-[3-(Benzyloxy)-1,1':4',1"-terphenyl-2'-yl]ethoxy}-1H-isoindole-1,3(2H)-dione A mixture of 2-[3-(benzyloxy)-1,1':4',1"-terphenyl-2'-yl]ethanol (2.046 g, 5.38 mmol), triphenylphosphine (1.707 g, 6.51 mmol) and N-hydroxyphthalimide (1.053 g, 6.45 mmol) was suspended in anhydrous tetrahydrofuran (30 mL) under nitrogen. The mixture was cooled in an ice/water bath. Diethyl azodicarboxylate (1.130 g, 6.49 mmol) was added drop wise. The mixture was stirred at room temperature overnight. The reaction mixture was evaporated to dryness. The residue was purified by flash chromatography (dichloromethane/hexanes) to give the title compound as a pale yellow waxy solid (2.509 g, 89%). $^1$H NMR (400 MHz, CDCl$_3$) 7.75-7.82 (m, 2H), 7.69-7.74 (m, 2H), 7.61-7.68 (m, 3H), 7.43-7.53 (m, 5H), 7.32-7.43 (m, 4H), 7.28 (d, J=8.0 Hz, 1H), 7.21 (t, J=7.9 Hz, 1H), 6.86-6.96 (m, 2H), 6.79 (dd, J=8.3, 1.9 Hz, 1H), 5.06 (s, 2H), 4.26 (t, J=7.6 Hz, 2H), 3.19 (t, J=7.5 Hz, 2H).

Production of O-{2-[3-(Benzyloxy)-1,1':4',1"-terphenyl-2'-yl]ethyl}hydroxylamine 2-{2-[3-(Benzyloxy)-1,1':4',1"-terphenyl-2'-yl]ethoxy}-1H-isoindole-1,3(2H)-dione (1.769 g, 3.37 mmol) was suspended in abs. ethanol (65 mL). Hydrazine hydrate (230 μL, 3.69 mmol) was added and the mixture heated at 65° C. under nitrogen for 8 h, then allowed to stand at room temperature overnight. The reaction mixture was filtered. The filter cake was washed with ethanol (2×30 mL). The combined filtrates were evaporated to dryness. The residue was suspended in dichloromethane (60 mL) and the mixture filtered. The filter cake was washed with dichloromethane (2×30 mL). The combined filtrates were evaporated to dryness. The residue was purified by flash chromatography (ethyl acetate/dichloromethane) to give the title compound as a clear oil (1.317 g, 99%). $^1$H NMR (400 MHz, CDCl$_3$) 7.59-7.68 (m, 2H), 7.55 (d, J=1.8 Hz, 1H), 7.42-7.52 (m, 5H), 7.27-7.42 (m, 6H), 6.93-7.03 (m, 3H), 5.22 (br. s, 2H), 5.11 (s, 2H), 3.77 (t, J=6.9 Hz, 2H), 2.96 (t, J=6.9 Hz, 2H).

Production of 2'-(2-Hydroxyethyl)-1,1':4',1"-terphenyl-3-ol (A56f)

A solution of O-{2-[3-(benzyloxy)-1,1':4',1"-terphenyl-2'-yl]ethyl}hydroxylamine (1.317 g, 3.33 mmol) in ethyl acetate (40 mL) was added to 10% palladium on carbon (346 mg, 0.33 mmol wrt Pd). The mixture was hydrogenated at 2.1 bar for 65 h. The mixture was filtered through celite. The filter cake was washed with ethyl acetate (2×40 mL). The combined filtrates were evaporated to dryness. The residue was purified by flash chromatography (methanol/dichloromethane) to give the title compound as a white powder (864 mg, 89%). $^1$H NMR (400 MHz, CDCl$_3$) 7.59-7.68 (m, 2H), 7.53-7.58 (m, 1H), 7.41-7.53 (m, 3H), 7.33-7.40 (m, 1H), 7.26-7.33 (m, 2H), 6.88-6.96 (m, 1H), 6.79-6.87 (m, 2H), 5.14 (br. s, 1H), 3.71-3.84 (m, 2H), 2.97 (t, J=6.8 Hz, 2H), 1.35-1.48 (m, 1H); HPLC (water/ACN+0.1% TFA gradient) 99.19% at 220 nm; LCMS [M+H—H$_2$O]$^+$=273.2, [M+Na]$^+$=313.2.

Production of 2-[2-(3-Hydroxy-1,1':4',1"-terphenyl-2'-yl)ethoxy]-1H-isoindole-1,3(2H)-dione (A56g)

A mixture of 2'-(2-hydroxyethyl)-1,1':4',1"-terphenyl-3-ol (864 mg, 2.98 mmol), triphenylphosphine (946 mg, 3.61 mmol) and N-hydroxyphthalimide (587 mg, 3.60 mmol) was suspended in anhydrous tetrahydrofuran (30 mL) under nitrogen. The mixture was cooled in an ice/water bath. Diethyl azodicarboxylate (626 mg, 3.59 mmol) was added dropwise. The mixture was stirred at room temperature overnight. The reaction mixture was evaporated to dryness. The residue was purified by flash chromatography (ethyl acetate/dichloromethane) to give the title compound as a white powder (1.265 g, 98%).

$^1$H NMR (400 MHz, CDCl$_3$) 7.79-7.88 (m, 2H), 7.71-7.79 (m, 2H), 7.56-7.68 (m, 3H), 7.41-7.54 (m, 3H), 7.31-7.40 (m, 2H), 7.23 (t, J=7.9 Hz, 1H), 6.93-7.00 (m, 1H), 6.88 (d, J=7.6 Hz, 1H), 6.75 (dd, J=8.1, 2.1 Hz, 1H), 5.72 (s, 1H), 4.40 (t, J=7.7 Hz, 2H), 3.21 (t, J=7.7 Hz, 2H); HPLC (water/ACN+0.1% TFA gradient) 98.52% at 220 nm; LCMS [M+Na]$^+$=458.1.

Production of 2'-[2-(Aminooxy)ethyl]-1,1':4',1"-terphenyl-3-ol (A56)

2-[2-(3-Hydroxy-1,1':4',1"-terphenyl-2'-yl)ethoxy]-1H-isoindole-1,3(2H)-dione (999 mg, 2.29 mmol) was suspended in abs. ethanol (45 mL). Hydrazine hydrate (150 µL, 2.40 mmol) was added. The mixture was heated at 65° C. for 4 h under nitrogen, then allowed to stand at room temperature overnight. The reaction mixture was filtered. The filter cake was washed with ethanol (2×20 mL). The combined filtrates were evaporated to dryness. The residue was suspended in dichloromethane (40 mL) and the mixture filtered. The filter cake was washed with dichloromethane (2×20 mL). The combined filtrates were evaporated to dryness. The residue was purified by flash chromatography (methanol/dichloromethane) to give the title compound as a white powder (648 mg, 92%). $^1$H NMR (400 MHz, CDCl$_3$) 7.60-7.66 (m, 2H), 7.54 (d, J=1.6 Hz, 1H), 7.41-7.51 (m, 3H), 7.33-7.39 (m, 1H), 7.26-7.32 (m, 1H), 6.89-6.96 (m, 1H), 6.79-6.87 (m, 2H), 5.29 (br. s, 3H), 3.82 (t, J=6.9 Hz, 2H), 2.98 (t, J=7.0 Hz, 2H); HPLC (water/ACN+0.1% TFA gradient) 95.36% at 220 nm; LCMS [M+H]$^+$=306.2, [M+Na]$^+$=328.1.

Example 5: Synthesis of A56k

Figure 5:
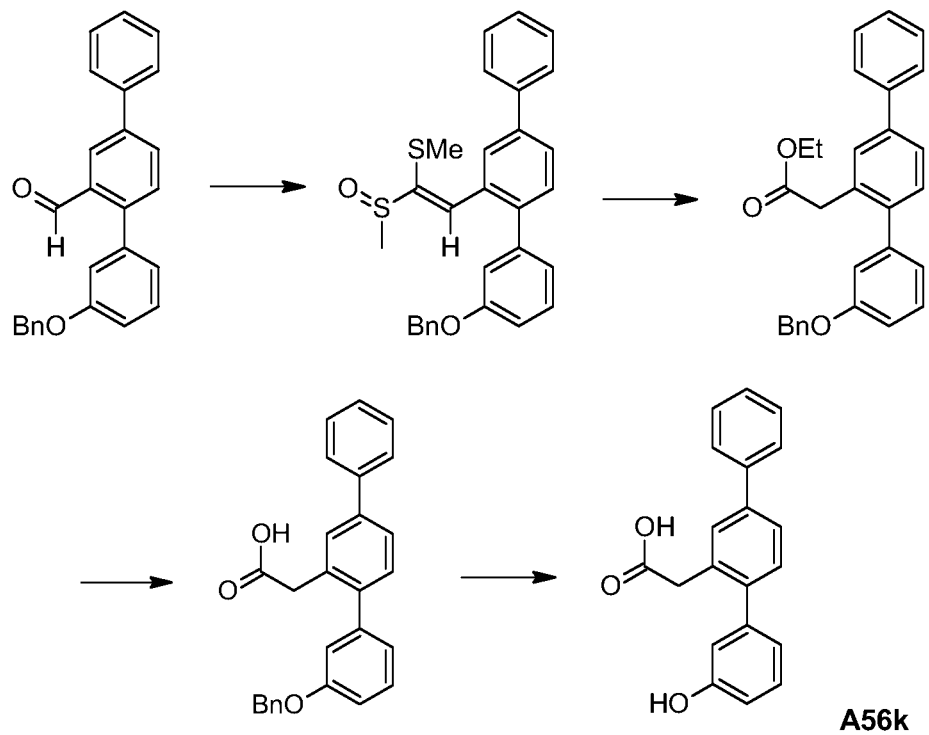
FIG. 5: Synthesis scheme for A56k.

The synthetic route used to prepare A56k is shown in FIG. 5.

Production of 2-[3-(Benzyloxy)-1,1':4',1"-terphenyl-2'-yl]-1-(methylsulfanyl)ethenyl methyl sulfoxide 3-(Benzyloxy)-1,1':4',1"-terphenyl-2'-carbaldehyde (5.330 g, 14.6 mmol) was dissolved in tetrahydrofuran (65 mL). Methyl (methylsulfinyl)methyl sulfide (2.745 g, 22.1 mmol) and sodium hydroxide (654 mg, 16.4 mmol) were added. The mixture was heated at reflux under nitrogen overnight. The reaction mixture was partitioned between ethyl acetate (400 mL) and water (200 mL). The aqueous layer was extracted with ethyl acetate (2×200 mL). The combined ethyl acetate layers were washed with water (2×200 mL) and brine (200 mL), dried over anhydrous sodium sulfate, and filtered. The filtrate was evaporated to dryness. The residue was purified by flash chromatography (ethyl acetate/dichloromethane) to give the title compound as a pale orange oil (3.733 g, 54%). $^1$H NMR (400 MHz, CDCl$_3$) 8.14 (d, J=1.4 Hz, 1H), 7.62-7.72 (m, 4H), 7.42-7.53 (m, 5H), 7.39 (t, J=7.3 Hz, 3H), 7.29-7.36 (m, 2H), 6.90-7.01 (m, 3H), 5.10 (s, 2H), 2.70 (s, 3H), 2.28 (s, 3H).

Production of Ethyl [3-(benzyloxy)-1,1':4',1"-terphenyl-2'-yl]acetate

2-[3-(Benzyloxy)-1,1':4',1"-terphenyl-2'-yl]-1-(methylsulfanyl)ethenyl methyl sulfoxide (3.733 g, 7.93 mmol) was dissolved in ethanol (70 mL). Conc. hydrochloric acid (6.6 mL) was added and the mixture heated at reflux for 5 days. The reaction mixture was partitioned between ethyl acetate (500 mL) and water (250 mL). The ethyl acetate layer was washed with water (200 mL) and brine (200 mL), dried over anhyd. sodium sulfate, and filtered. The filtrate was evaporated to dryness. The residue was purified by flash chromatography (dichloromethane) to give the title compound as a yellow-orange oil (2.129 g, 64%). $^1$H NMR (400 MHz, CDCl$_3$) 7.60-7.68 (m, 2H), 7.59 (br. s, 1H), 7.55 (dd, J=8.0, 1.6 Hz, 1H), 7.42-7.50 (m, 4H), 7.29-7.42 (m, 6H), 6.92-7.04 (m, 3H), 5.09 (s, 2H), 4.10 (q, J=7.0 Hz, 2H), 3.65 (s, 2H), 1.21 (t, J=7.1 Hz, 3H); LCMS [M+H]$^+$=423.1.

Production of [3-(Benzyloxy)-1,1':4',1"-terphenyl-2'-yl]acetic acid

Ethyl [3-(benzyloxy)-1,1':4',1"-terphenyl-2'-yl]acetate (414 mg, 0.98 mmol) was dissolved in ethanol (15 mL). Sodium hydroxide solution (1M, 3 mL, 3 mmol) was added and the mixture heated at 70° C. for 1 h. The reaction mixture was partitioned between ethyl acetate (45 mL) and hydrochloric acid (1M, 15 mL). The ethyl acetate layer was washed with water (15 mL) and brine (15 mL), dried over anhydrous sodium sulfate, and filtered. The filtrate was evaporated to dryness to give the title compound as a pale brown powder (350 mg, 91%). $^1$H NMR (400 MHz, CDCl$_3$) 7.59-7.65 (m, 2H), 7.53-7.59 (m, 2H), 7.40-7.48 (m, 4H), 7.27-7.39 (m, 6H), 6.96-7.02 (m, 2H), 6.91-6.96 (m, 1H), 5.08 (s, 2H), 3.68 (s, 2H).

Production of (3-Hydroxy-1,1':4',1"-terphenyl-2'-yl)acetic acid (A56k)

[3-(Benzyloxy)-1,1':4',1"-terphenyl-2'-yl]acetic acid (350 mg, 0.89 mmol) was suspended in acetic acid (9 mL) and conc. hydrochloric acid (2.2 mL). The mixture was heated at 100° C. for 2.25 h. The reaction mixture was poured into water (60 mL) and the mixture extracted with ethyl acetate (60 mL). The ethyl acetate layer was washed with water (2×30 mL) and brine (30 mL), dried over anhydrous sodium sulfate, and filtered. The filtrate was evaporated to dryness. The residue was suspended in toluene (20 mL) and evaporated to dryness. This process was repeated. The residue was purified by flash chromatography (ethyl acetate/dichloromethane) to give the title compound as a waxy brown solid (189 mg, 70%). The product was suspended in 7.5% dichloromethane/hexanes and isolated by filtration to give a pale beige powder. $^1$H NMR (400 MHz, CDCl$_3$) 7.58-7.65 (m, 2H), 7.51-7.58 (m, 2H), 7.40-7.48 (m, 2H), 7.31-7.39 (m, 2H), 7.26-7.30 (m, 1H), 6.87-6.92 (m, 1H), 6.79-6.86 (m, 2H), 3.69 (s, 2H); HPLC (water/ACN+0.1% TFA gradient) 95.58% at 220 nm; LCMS [M−H]$^-$=303.1, [2M−H]$^-$=607.3.

Example 6: Synthesis of Intermediate A31-4

Figure 6:
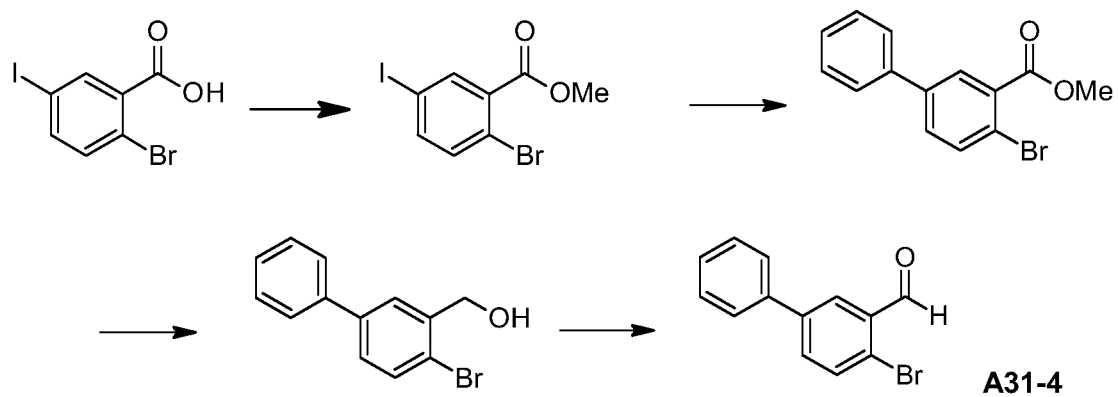
FIG. 6: Synthesis scheme for Intermediate A31-4.

The synthetic route used to prepare A31-4 is shown in FIG. 6.

Production of Methyl 2-bromo-5-iodobenzoate

A mixture of 2-bromo-5-iodobenzoic acid (20.070 g, 61.4 mmol) and potassium carbonate (12.698 g, 91.9 mmol) was suspended in DMF (45 mL). Iodomethane (11.373 g, 80.1 mmol) was added and the mixture stirred at room temperature overnight. The reaction mixture was partitioned between diethyl ether (400 mL) and water (250 mL). The ether layer was washed with water (2×120 mL) and brine (120 mL), dried over anhydrous sodium sulfate, and filtered. The filtrate was evaporated to dryness to give the title compound as an orange oil (20.451 g, 98%). $^1$H NMR (400 MHz, CDCl$_3$) 8.10 (d, J=2.0 Hz, 1H), 7.62 (dd, J=8.4, 2.1 Hz, 1H), 7.38 (d, J=8.2 Hz, 1H), 3.93 (s, 3H). [Reference: WO 2004/048314].

Production of Methyl 4-bromobiphenyl-3-carboxylate

Methyl 2-bromo-5-iodobenzoate (10.019 g, 29.4 mmol), phenylboronic acid (3.571 g, 29.3 mmol) and potassium carbonate (8.112 g, 58.7 mmol) were dissolved in a mixture of toluene (200 mL), abs. ethanol (50 mL) and water (25 mL). The reaction flask was purged with nitrogen and nitrogen bubbled through the mixture for 30 min. Tetrakis(triphenylphosphine)palladium (3.401 g, 2.94 mmol) was added under a stream of nitrogen. Nitrogen was bubbled through the reaction mixture for 15 min. The mixture was heated at reflux for 12 h, then allowed to stand at room temperature. The reaction mixture was partitioned between toluene (100 mL) and water (300 mL). The aqueous layer was extracted with toluene (100 mL). The combined toluene layers were washed with brine (150 mL), dried over anhydrous sodium sulfate and filtered. The filtrate was evaporated to dryness. The residue was purified by flash chromatography (dichloromethane/hexanes) to give the title compound as an orange oil (8.092 g, 84%).

$^1$H NMR (400 MHz, CDCl$_3$) 8.01 (d, J=2.3 Hz, 1H), 7.72 (d, J=8.4 Hz, 1H), 7.52-7.60 (m, 3H), 7.43-7.49 (m, 2H), 7.36-7.42 (m, 1H), 3.96 (s, 3H).

Production of (4-Bromobiphenyl-3-yl)methanol

A solution of methyl 4-bromobiphenyl-3-carboxylate (6.992 g, 24.0 mmol) in anhydrous tetrahydrofuran (80 mL) was prepared under nitrogen. A suspension of lithium aluminium hydride (692 mg, 18.2 mmol) in anhyd. tetrahydrofuran (60 mL) was prepared under nitrogen and cooled in an ice/water bath. The ester solution was transferred to the lithium aluminium hydride suspension via cannula. The mixture was stirred in the ice/water bath for 40 min. The excess lithium aluminium hydride was quenched by the drop wise addition of water (1.75 mL), 15% sodium hydroxide solution (1.75 mL) and water (7 mL). The mixture was stirred at room temperature for 40 min. Ethyl acetate (290 mL) was added and the mixture filtered through celite. The filter cake was washed with ethyl acetate (2×140 mL). The combined filtrates were evaporated to dryness. The residue was combined with the crude products from similar reactions with methyl 4-bromobiphenyl-3-carboxylate (1.024 g, 3.51 mmol), and the mixture purified by flash chromatography (dichloromethane/hexanes) to give the title compound as a pale orange oil which solidified on standing (6.729 g, 93%). $^1$H NMR (400 MHz, CDCl$_3$) 7.71 (d, J=2.1 Hz, 1H), 7.53-7.64 (m, 3H), 7.41-7.48 (m, 2H), 7.32-7.41 (m, 2H), 4.82 (d, J=6.4 Hz, 2H), 2.01 (t, J=6.4 Hz, 1H).

Production of 4-Bromobiphenyl-3-carbaldehyde (A31-4)

Activated manganese(IV) oxide (19.279 g, 222 mmol) was added to a solution of (4-bromobiphenyl-3-yl)methanol (5.844 g, 22.2 mmol) in toluene (90 mL). The mixture was stirred at 60° C. under nitrogen for 16 h. The reaction mixture was filtered through celite. The filter cake was washed with toluene (2×20 mL). The combined filtrates were evaporated to dryness to give the title compound as a pale yellow oil which solidified on standing (4.782 g, 82%). $_1$H NMR (400 MHz, CDCl$_3$) 10.41 (s, 1H), 8.14 (d, J=2.1 Hz, 1H), 7.70-7.74 (m, 1H), 7.65-7.70 (m, 1H), 7.56-7.63 (m, 2H), 7.43-7.51 (m, 2H), 7.36-7.43 (m, 1H).

Example 7: Synthesis of A26 and A27

Figure 7:
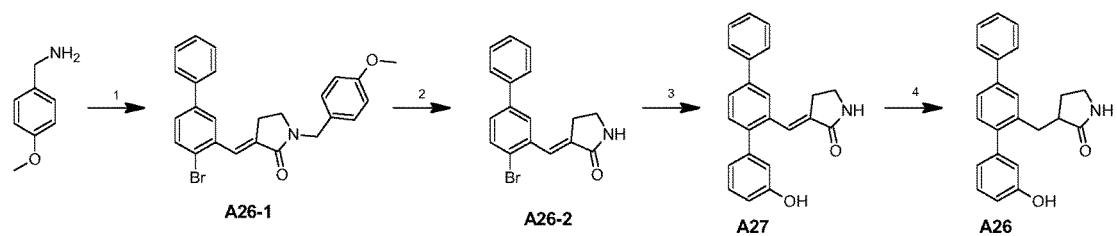
FIG. 7: Synthesis scheme for A26 and A27.

The synthetic route used to prepare A26 and A27 is shown in FIG. 7.

Step 1—i) 1-Carboethoxycyclopropyl triphenylphosphonium tetrafluoroborate, DMF, 2 h, 80° C., ii) A31-4, 18 h, 80° C. (adapted from Chung et al Org. Letts, 2011 Vol. 13, No. 19, 5338-5341).

Step 2—TFA, DCM (adapted from WO2009/89359).

Step 3—3-Hydroxybenzeneboronic acid, K$_2$CO$_3$, H$_2$O, 1,4-dioxane, Pd(PPh$_3$)$_4$, 18 h, 75° C.

Step 4—H$_2$ (balloon), 5 mol % Pd/C in MeOH, 18 h, 50° C. (adapted from WO2005/90300).

Example 8: Synthesis of A31

Figure 8:
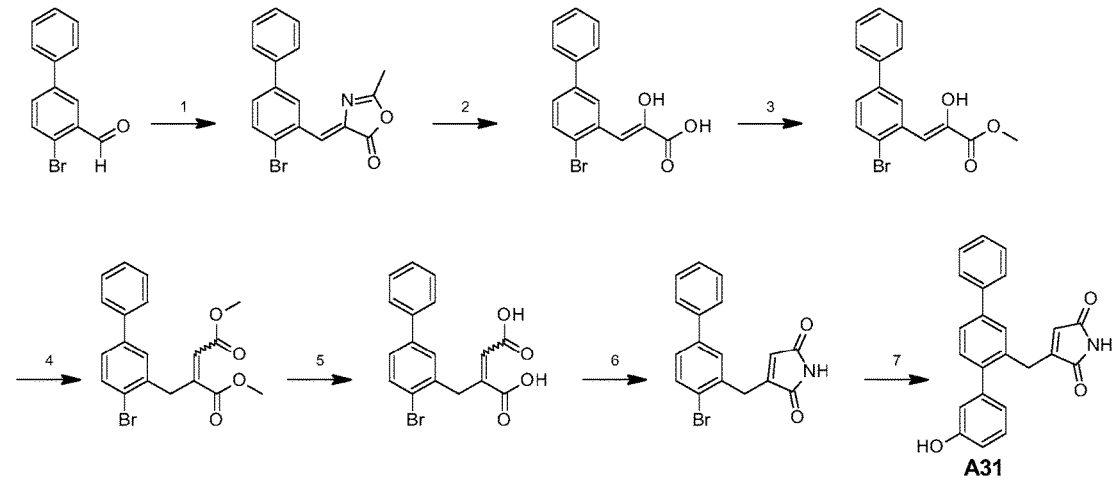
FIG. 8: Synthesis scheme for A31.

The synthetic route used to prepare A31 is shown in FIG. 8.

Step 1—N-Acylglycine, Ac$_2$O, AcONa, heat, 6 h.

Step 2—3M HCl, heat

Step 3—MeI, DBU, DMF, heat.

Step 5—Methoxycarbonylmethyltriphenylphosphorane, toluene to give a mixture of E and Z-isomers Step 5—NaOH, heat (Steps 1-5 adapted from Wong et al, Synthesis, 1992, 793-797 and Queffe'lec et al, Eur. J. Chem., 2008, 43(10), 2268-2271).

Step 6—Urea, toluene, heat. (E-isomer to remain unreacted—as described in WO2008/15139)

Step 7—3-Hydroxybenzeneboronic acid, K$_2$CO$_3$, H$_2$O, 1,4-dioxane, Pd(PPh$_3$)$_4$, 18 h, 75° C.

Example 9: Synthesis of A35

Figure 9:
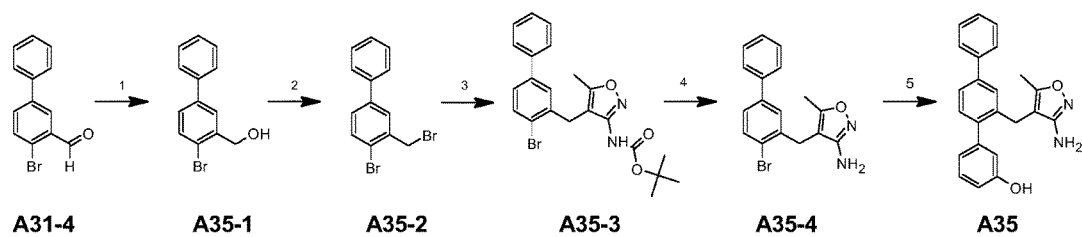
FIG. 9: Synthesis scheme for A35.

The synthetic route used to prepare A35 is shown in FIG. 9.
Step 1—NaBH$_4$, MeOH, rt.
Step 2—PBr$_3$, THF (as described in Yu et al, Org. Letts, 2009, vol. 11(2), 469-472).
Step 3—(4-Formyl-5-methyl-isoxazol-3-yl)-carbamic acid tert-butyl ester, nBuLi, THF (as described in Konoike et al Tet. Letts, Vol. 37, No. 19, 3339-3342, 1996).
Step 4—TFA, DCM, rt
Step 5—3-Hydroxybenzeneboronic acid, K$_2$CO$_3$, H$_2$O, 1,4-dioxane, Pd(PPh$_3$)$_4$, 18 h, 75° C.

Example 10: Synthesis of A45

Figure 10:
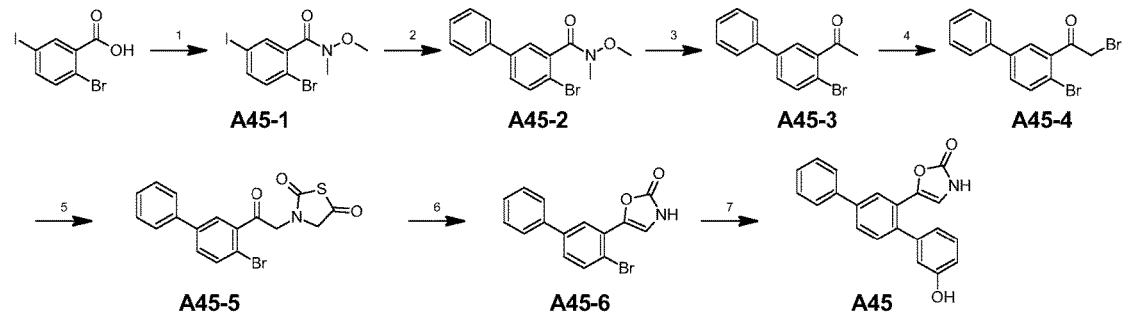
FIG. 10: Synthesis scheme for A45.

The synthetic route used to prepare A45 is shown in FIG. 10.
Step 1—HNMeOMe.HCl, CDI, DIPEA, DCM (adapted from WO2011/119518)
Step 2—Benzeneboronic acid, Pd(PPh$_3$)$_4$, K$_2$CO$_3$, Toluene:ethanol:water, heat, 12 h.
Step 3—MeMgBr, THF, 0° C. (as described in EP2455380)
Step 4—Br$_2$, EtOH, rt (as described in WO2008/157726)
Step 5—1,3-thiazolidine-2,4-dione, K$_2$CO$_3$, TBAI, DMF, rt, 2 h (adapted from Nagarapu et al, Euro. J. Med. Chem. 71, (2014), 91-97)
Step 6—NaOH in MeOH or NEt$_3$ in EtOH) (adapted from Shvaika et al, J. Org. Chem. USSR, 1983, vol. 19, #8, 1533-1543)
Step 7—3-Hydroxybenzeneboronic acid, K$_2$CO$_3$, H$_2$O, 1,4-dioxane, Pd(PPh$_3$)$_4$, 18 h, 75° C.

Example 11: Synthesis of A79

Figure 11:
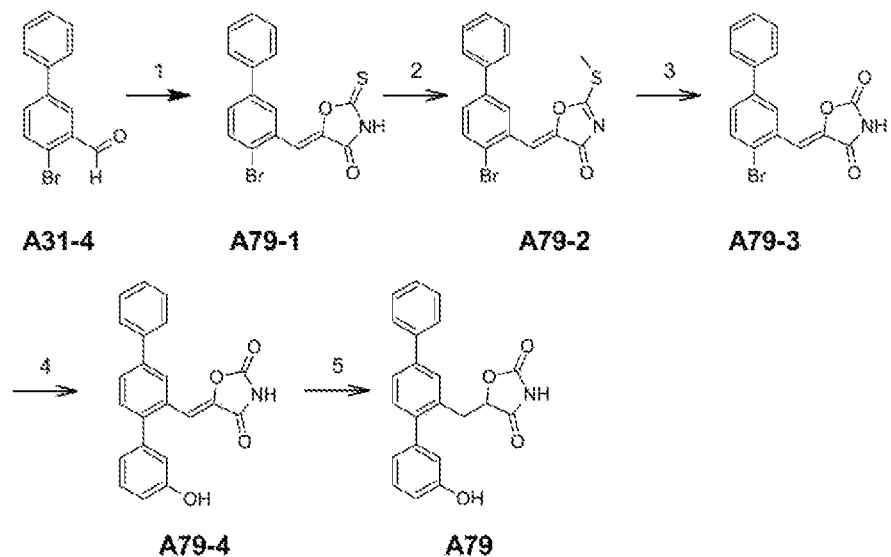
FIG. 11: Synthesis scheme for A79.

The synthetic route used to prepare A79 is shown in FIG. 11.
Step 1—4-Oxazolidinon-2-thione, NaOAc, HOAc.
Step 2—MeI, (i-Pr)$_2$NEt
Step 3—HCl, EtOH, H$_2$O
(Steps 1-3 adapted from Unangst et al, J. Med. Chem. 1994, 37, 322-328).
Step 4—3-Hydroxybenzeneboronic acid, K$_2$CO$_3$, H$_2$O, 1,4-dioxane, Pd(PPh$_3$)$_4$, 18 h, 75° C.
Step 5—H$_2$ (balloon), 5 mol % Pd/C in MeOH, 18 h, 50° C.

Example 12: Synthesis of A81

Figure 12:
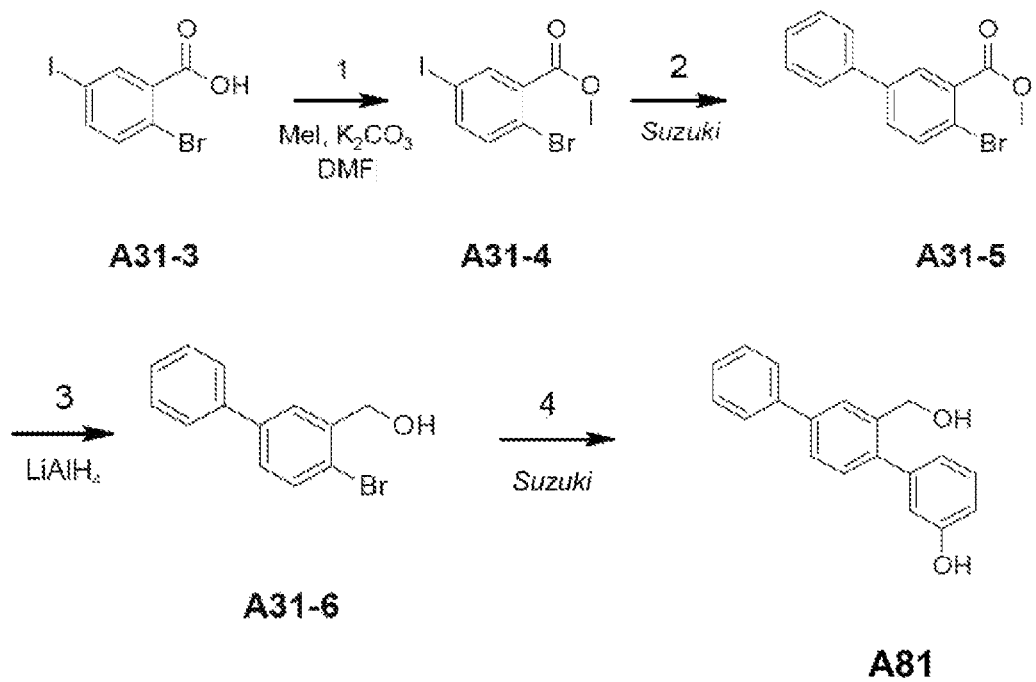
FIG. 12: Synthesis scheme for A81.

The synthetic route used to prepare A81 is shown in FIG. 12.
Step 1:
i) 5.02 g A31-3 gave desired product A31-4 (5.027 g, 96% yield).
ii) 20.1 g, mol A31-3 gave desired product A31-4 (20.451 g, 98% yield)
Step 2:
i) 0.984 g A31-4 (1.0 equiv PhB(OH)$_2$, 0.05 equiv Pd(dppf)Cl$_2$, 2 equiv K$_2$CO$_3$, Dioxane/ethanol/water, 85° C., 16 h). Complete consumption of A31-4 observed by TLC. Crude product was fractionated by column chromatography. Pure samples were not obtained but at least 4 products, including a biphenyl consistent with A31-5 were detected by 1H NMR analysis.
ii) 10 g A31-4 gave desired product A31-5 (8.1 g, 84%)
Step 3:
i) 0.809 g A31-5 (1.5 equiv LiAlH$_4$, r.t., 16 h) gave desired product A31-6 (0.340 g, 47%) and the undesired des-bromo compound (biphenyl-3-ylmethanol): 0.208 g, 41%.
ii) 0.510 g A31-5 (1.5 equiv LiAlH$_4$, 0° C., 50 min) gave desired product (crude) A31-6 (0.435 g, 95%). Contained 10 mol % of the des-bromo compound by 1H NMR. Purification with larger scale batch pending.
iii) 0.514 g A31-5 (0.75 equiv LiAlH$_4$, 0° C., 50 min) gave desired product (crude) A31-6 (0.453 g, 98%). Contained 5.5 mol % of the des-bromo compound by 1H NMR.
iv) 6.992 g A31-5 (0.75 equiv LiAlH$_4$, 0° C., 40 min) gave crude product A31-6 (6.183 g) containing 5.5 mol % of the des-bromo compound by 1H NMR. Combined with products from two trial reactions purified by column chromatography to give A31-6 (6.729 g, 93%).
Step 4:
0.102 g A31-6 (1.2 equiv 3-(HO)C$_6$H$_4$B(OH)$_2$, 0.1 equiv Pd(PPh$_3$)$_4$, 3 equiv K$_2$CO$_3$, toluene/ethanol/water, Δ, 17 h) gave desired product A81 (0.054 g, 50% yield).

Example 13: In Vitro Screening of Compounds

The xCELLigence SP system (Roche) was used to measure changes in cellular impedance (cell index) following the treatment of bovine aortic endothelial cells (European Collection of Cell Cultures) with test compound. In this in vitro cell based experimental system a negative impedance profile correlates with blood pressure reduction in rats—a decrease in impedance is associated with vasodilatation and an increase in impedance is associated with vasoconstriction (Stallaert W, Dorn J F, van der Westhuizen E, Audet M & Bouvier M. Impedance responses reveal β-adrenergic signaling pluridensitometry and allow classification of ligands with distinct signalling profiles PLoS ONE 2012; 7(1): e29420, doi:10.1371/journal.pone.0029420).

Briefly, 50 µl of cell culture medium (DMEM low glucose supplemented with 15% fetal bovine serum at 37° C.) was added to each well of an E-Plate 96 (Roche), and the background impedance in each well was measured. 50 µl of bovine aortic endothelial cell suspension (10,000 cells/well) was then added to the appropriate wells of the E-Plate 96. Cell index was monitored for each well of the E-Plate 96 in RTCA SP Station within the cell culture incubator. After overnight incubation for 16-20 hours at 5% CO$_2$ and 95% humidity, 100 µl of test compound solution (test compounds were prepared in DMSO and diluted with cell culture medium to a concentration of 62.5 µM, 125 µM or 250 µM of test compound with a final DMSO concentration of 0.25%) was added to the appropriate wells of the E-Plate 96 and cell index values were measured immediately following compound treatment every 20 seconds for 3 hours. Cell index value is baseline-corrected by subtracting the cell index of vehicle-treated cells and normalized by dividing by the cell index at the time point immediately before compound addition. Baseline normalized cell index as a function of time is plotted using Roche RTCA software.

Figure 13:
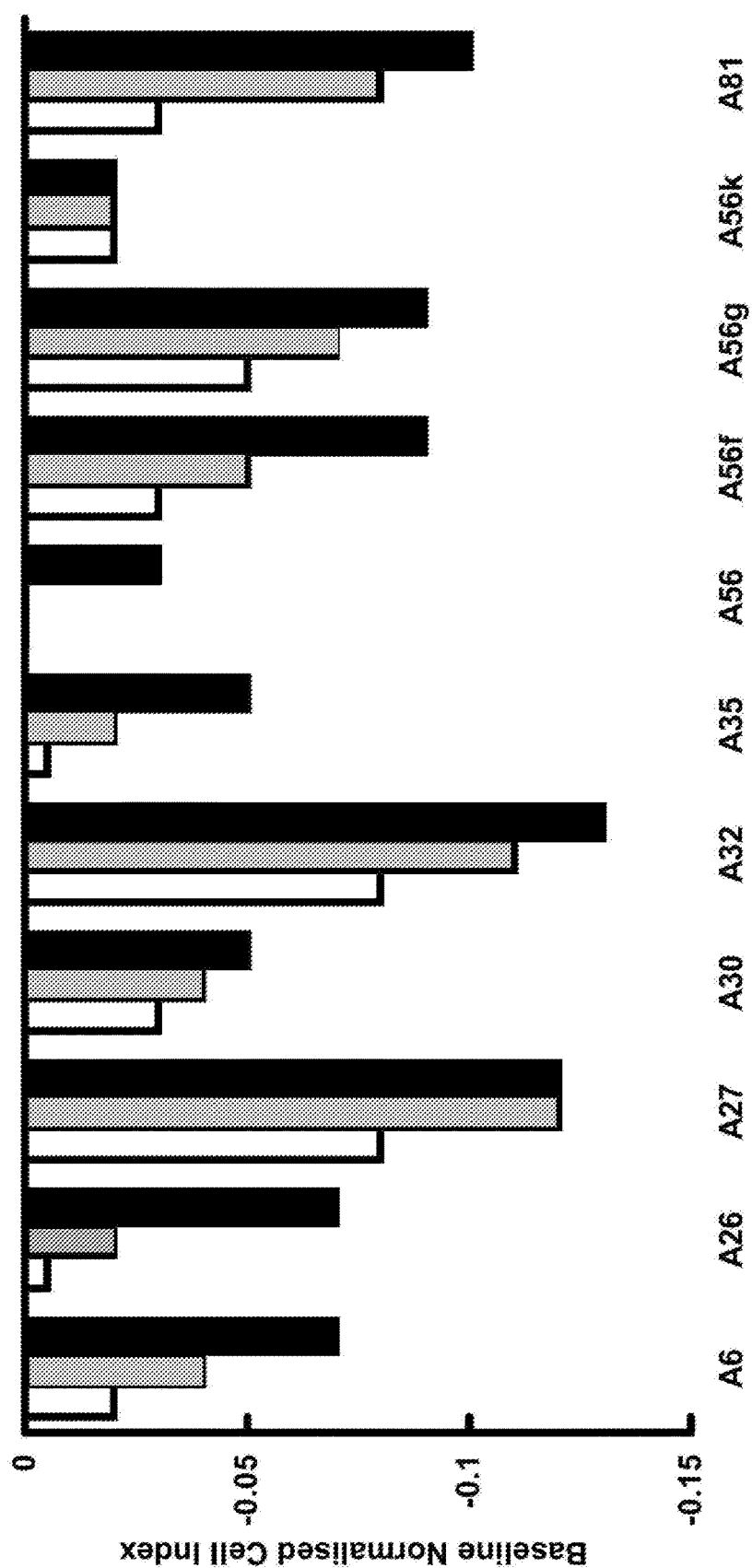
FIG. 13: Cell impedance in bovine aortic endothelial cells treated with test compounds at 3 concentrations 62.5 µM (white bars), 125 µM (grey bars) and 250 µM (black bars).

Negative impedance responses for bovine aortic endothelial cells were observed for A6, A26, A27, A30, A32, A35, A56, A56f, A56g, A56k and A81 (FIG. 13), indicating that these compounds are vasodilators.

Human (HPCT-wt-05) and rat (NRK-52E) renal proximal tubule cells grown in (Keratinocyte Medium II+Keratinocyte Growth Supplement+5 ng/ml human recombinant epidermal growth factor+5% FBS+2 mM glutamine or DMEM+10% FBS+1% NEAA+2 mM glutamine respectively) were placed in 96 well plates at 10,000 cells/well and incubated at 37° C. with 5% CO$_2$ overnight. Test compounds at concentrations of 32 µM or 63 µM were incubated with human or rat renal proximal tubule cells for 2 hours at 37° C. and 5% $CO_2$. Cis-diamminedichloroplatinum(III) (cisplatin) was then added at a concentration of 5 µg/ml for human cells and 12.5 µg/ml for rat cells. Each cell population was then incubated for 24 hours at 37° C. with 5% $CO_2$. Test compound A32 was maintained at its original concentrations. To assay the cytotoxic effects of cisplatin on the human and rat renal proximal tubule cells a highly water-soluble tetrazolium salt, WST-8, which is reduced by dehydrogenases in cells to produce formazan, a water-soluble, yellow-coloured indicator dye was used following the manufacturer's instructions (specifically the Cell Count Kit-8 (CCK-8) assay from Sigma). Plate absorbance of the WST-8 (CCK-8) reagent was then measured at 450 nm using a Thermo Scientific Multiskan EX plate reader.

Figure 14:
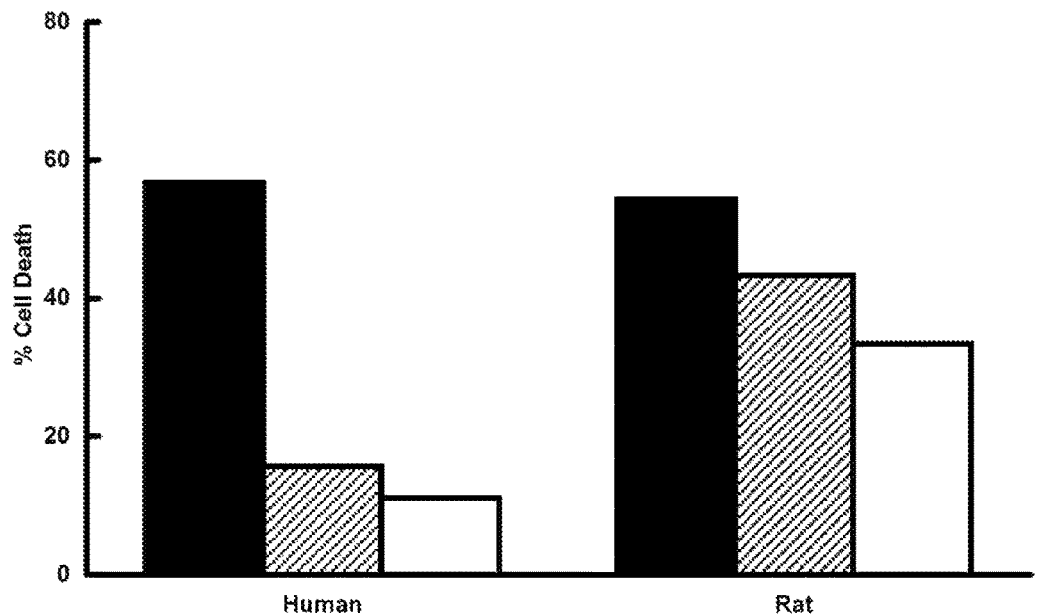
FIG. 14: Cell death in human renal proximal tubular cells incubated with cis-diamminedichloroplatinum (III) (cisplatin) 5 µg/ml alone (solid bars), cisplatin 5 µg/ml plus 32 µM of A32 (hatched bars), cisplatin 5 µg/ml plus 63 µM of A32 (open bars) and cell death in rat renal proximal tubular cells incubated with cisplatin 12.5 µg/ml alone (solid bars), cisplatin 12.5 µg/ml plus 32 µM of A32 (hatched bars), cisplatin 12.5 µg/ml plus 63 µM of A32 (open bars). All incubations were 24 hrs duration.

Cisplatin induced cell death was decreased in cultures of human and rat renal proximal tubular cells treated with 32 µM or 63 µM of A32 for 24 hours (FIG. 14), demonstrating that this compound reduces renal proximal tubular cell death.

Example 14: In Vivo Screening of Compounds

Fourteen week old SHR on a 2.2% salt diet (Glen Forrest Stockfeeders) were randomly assigned to zero time control, test compound treatment (500 pmol/kg/min) in the drinking solution or control drinking solution (5% ethanol in deionised distilled water (n=5 each group). The rats assigned to zero time control group (14 weeks old rats) were anaesthetised and had their kidneys and heart harvested while rats assigned to control and test compound treatment were weighed twice weekly and had their drinking solution intake monitored to allow adjustment of the test compound concentration in the drinking solution to maintain a constant dose over the 4-week study period (18 weeks old rats). At the completion of the study period, rats were anaesthetised and had their kidneys and heart harvested.

Fourteen week old SHR on a high fat diet (Glen Forrest Stockfeeders) were randomly assigned to test compound drinking solution (500 pmol/kg/min test compound in 10% ethanol in deionised distilled water) or control drinking solution (10% ethanol in deionised distilled water). After 4 weeks, rats were anaesthetised and blood samples were taken for analysis of plasma aminotransferase (AST) levels and livers were harvested.

To quantitate tissue fibrosis and/or fat content, tissue slices≤3 mm thick were fixed in 10% buffered formalin for 24 hours, processed and embedded in paraffin. Three micron transverse sections were stained using Masson's trichrome stain. A minimum of 20 random fields at magnification×20 from transverse sections (5 at each of 2 levels) were digitized and the degree of fibrosis determined as a percent of field area of each digitized image using Image-Pro Plus V.7 (Media Cybernetics, Bethesda, Md., USA) then averaged to determine the level of fibrosis and/or fat content for each rat.

Plasma AST levels were measured using a RefloVET Plus (Roche) machine using consumable strips with magnetic assay identifiers recognized by the machine. A calibration standard was used in the machine prior to each use and the device was operated according to the manufacturer's instructions. Results are presented as international units per liter (IU/L).

Figure 15:
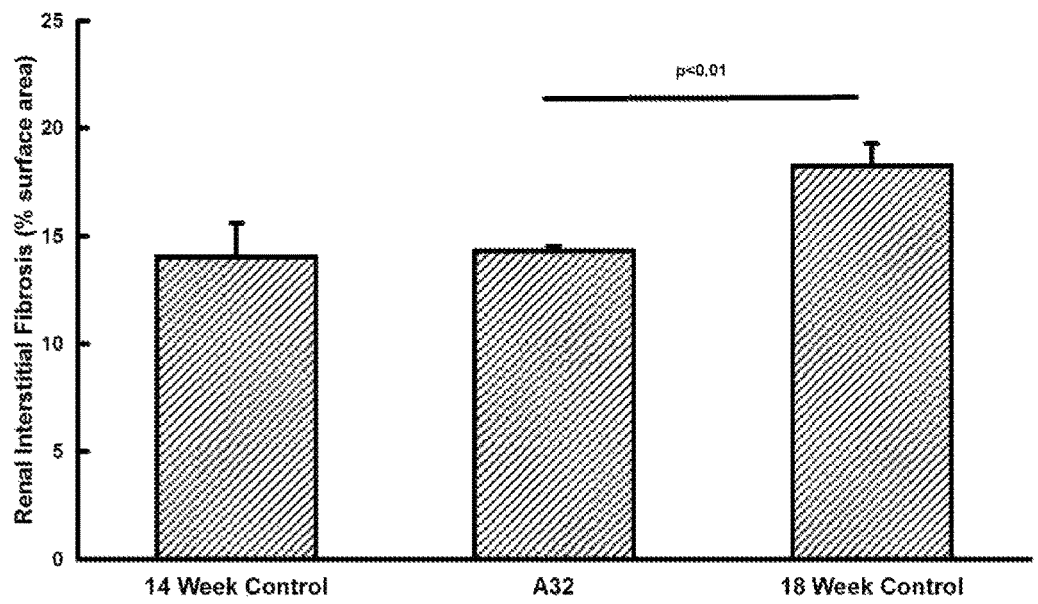
FIG. 15: Effect of 500 pmol/kg/min of A32 for 4 weeks on interstitial fibrosis in the kidney in SHR on 2.2% salt diet and 5% ethanol drinking solution.

Fibrosis in the kidney after 4 weeks treatment with 500 pmol/kg/min of A32 was decreased compared to 18 week controls (FIG. 15), demonstrating that this compound prevents the development of kidney fibrosis.

Figure 16:
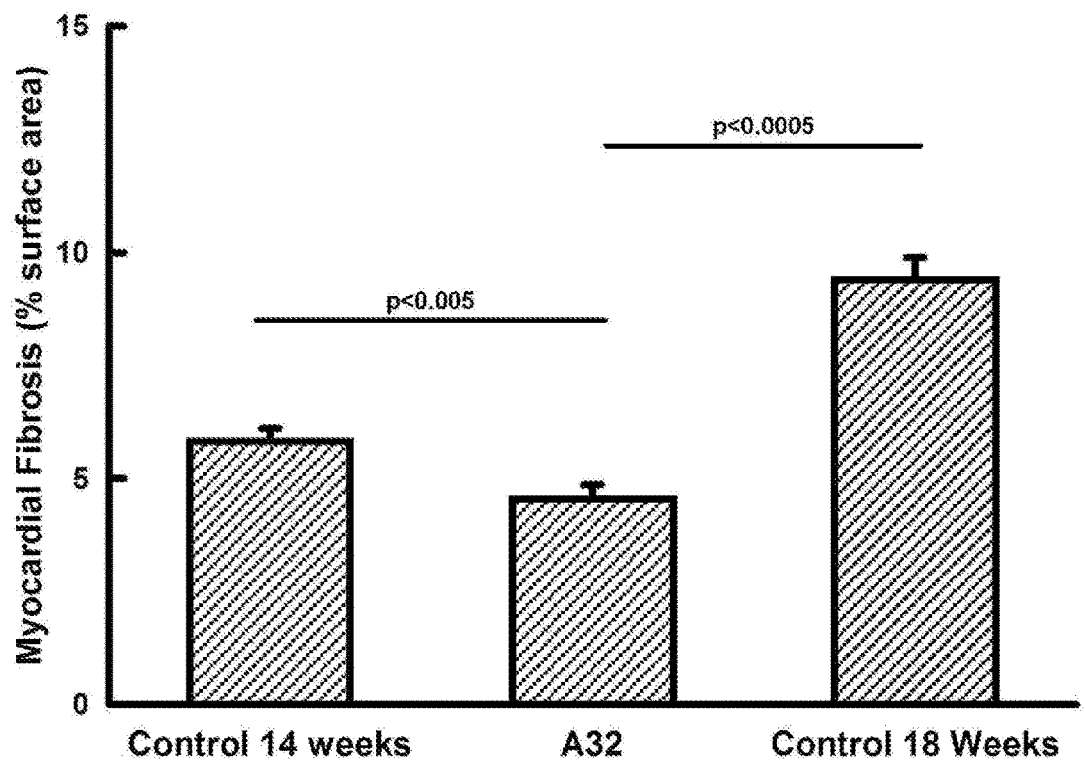
FIG. 16: Effect of 500 pmol/kg/min of A32 for 4 weeks on myocardial fibrosis in SHR on 2.2% salt diet and 5% ethanol drinking solution.

Myocardial fibrosis after 4 weeks treatment with 500 pmol/kg/min of A32 was decreased compared to 14 and 18 week controls (FIG. 16), demonstrating that this compound prevents the development of myocardial fibrosis and reverses established myocardial fibrosis.

Figure 17:
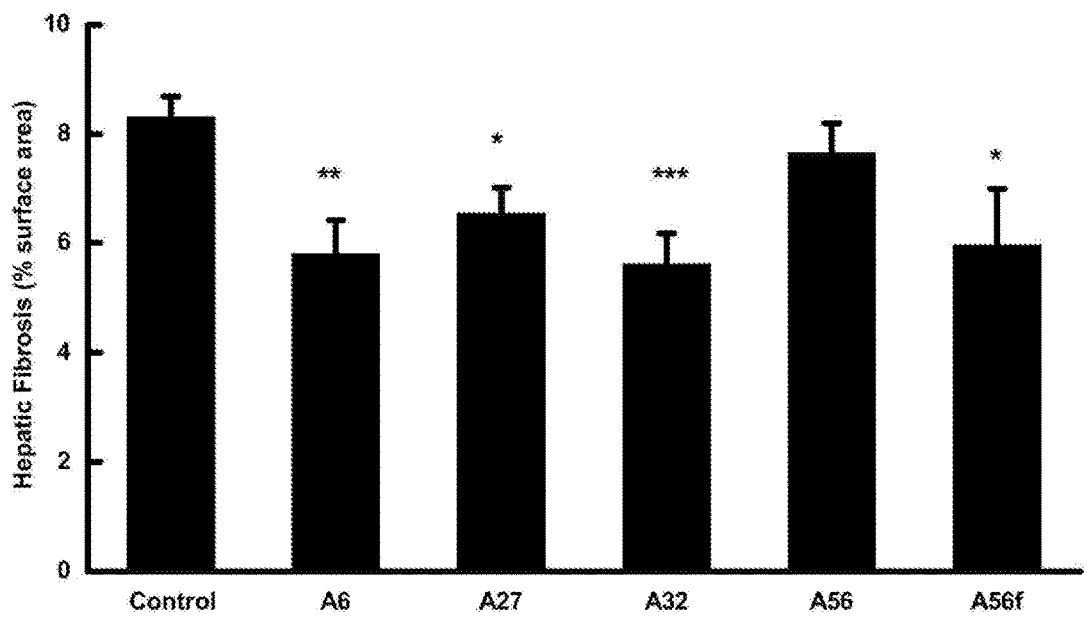
FIG. 17: Effect of 500 pmol/kg/min of A32 for 6 weeks on hepatic fibrosis in SHR on high fat diet and 10% ethanol drinking solution.

Hepatic fibrosis after 6 weeks treatment with 500 pmol/kg/min of A6, A27, A32 and A56f was decreased compared controls (FIG. 17, *p<0.025, p<0.01, *p<0.005), demonstrating that these compounds prevent the development of hepatic fibrosis.

Figure 18:
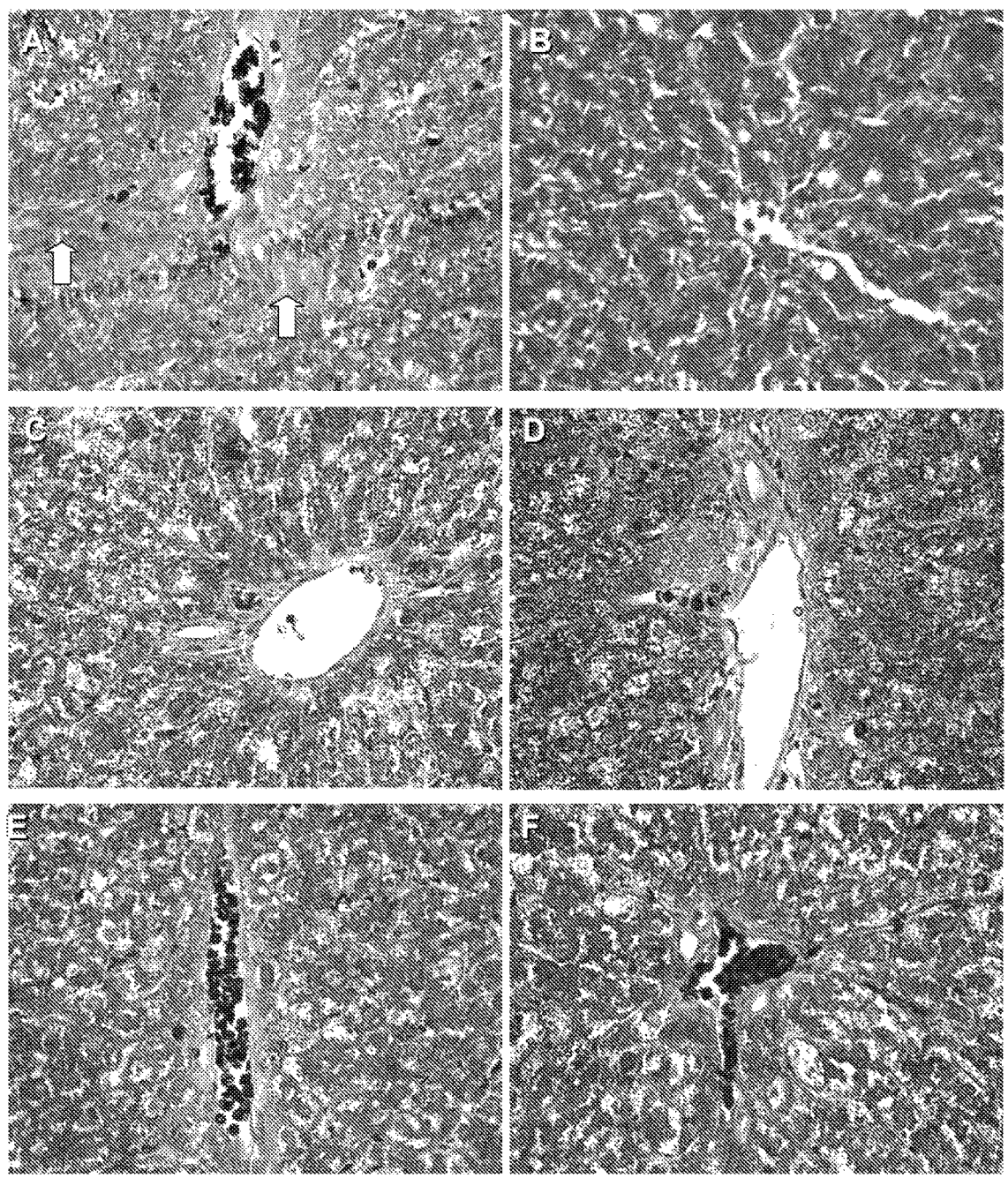
FIG. 18: Masson's tri-chrome stained sections showing portal tracts from control rats (A), as well as rats treated with A32 (B), A6 (C), A27 (D), A56 (E) and A56f (F).

In Masson's tri-chrome stained sections showing portal tracts, fibrous bands can be seen extending from the portal tract (arrows) and disrupting tissue architecture in the control (FIG. 18A). In sections from rats treated with A32 (FIG. 18B), A6 (FIG. 18C), A27 (FIG. 18D), A56 (FIG. 18E) and A56f (FIG. 18F), normal tissue architecture has been restored.

Figure 19:
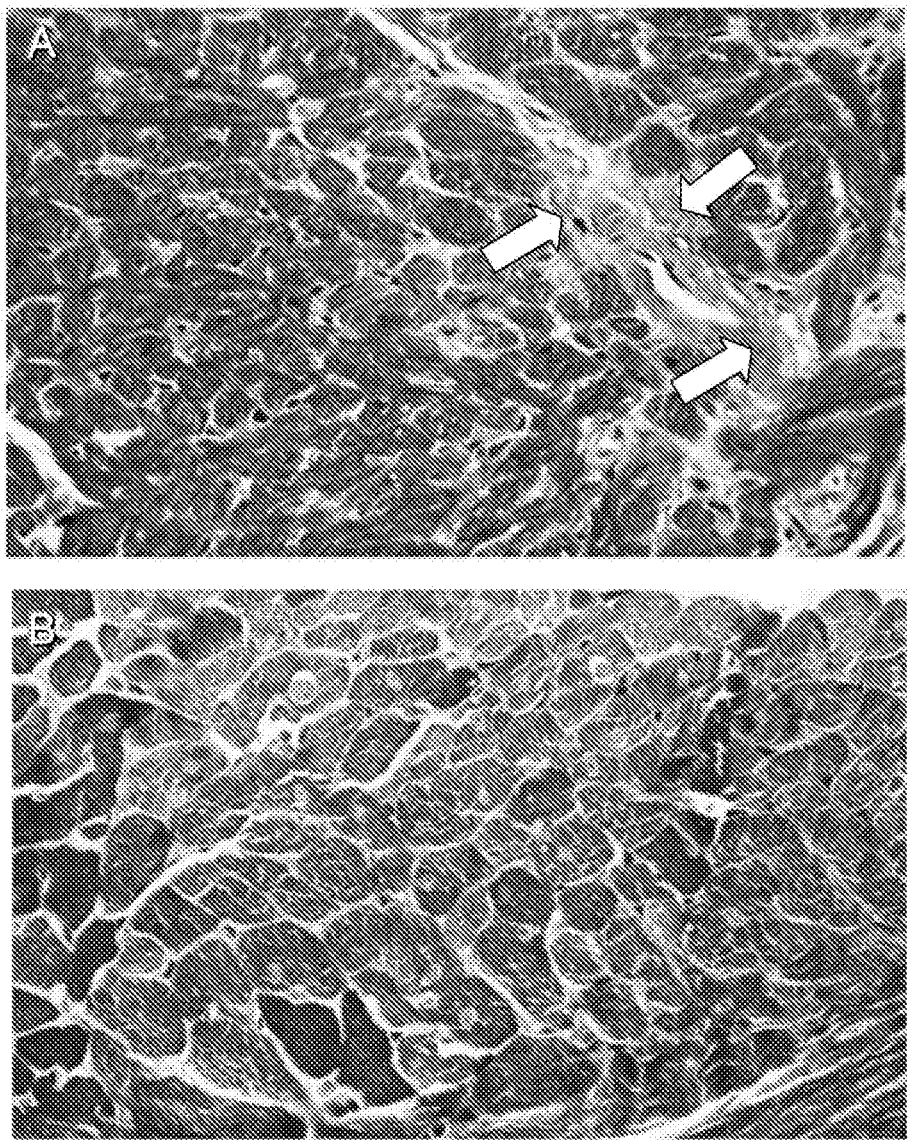
FIG. 19: Masson's tri-chrome stained sections showing heart tissue from control rats (A) and rats treated with A32 (B)

In Masson's tri-chrome stained sections showing heart tissue from control rats (FIG. 19A), fibrosis is present throughout the section interspersed between muscle fibres, in some instances surrounding and replacing muscle fibres (arrows). In sections showing heart tissue from rats treated with A32 (FIG. 19B), minimal fibrous tissue is present and normal tissue architecture has been restored.

Figure 20:
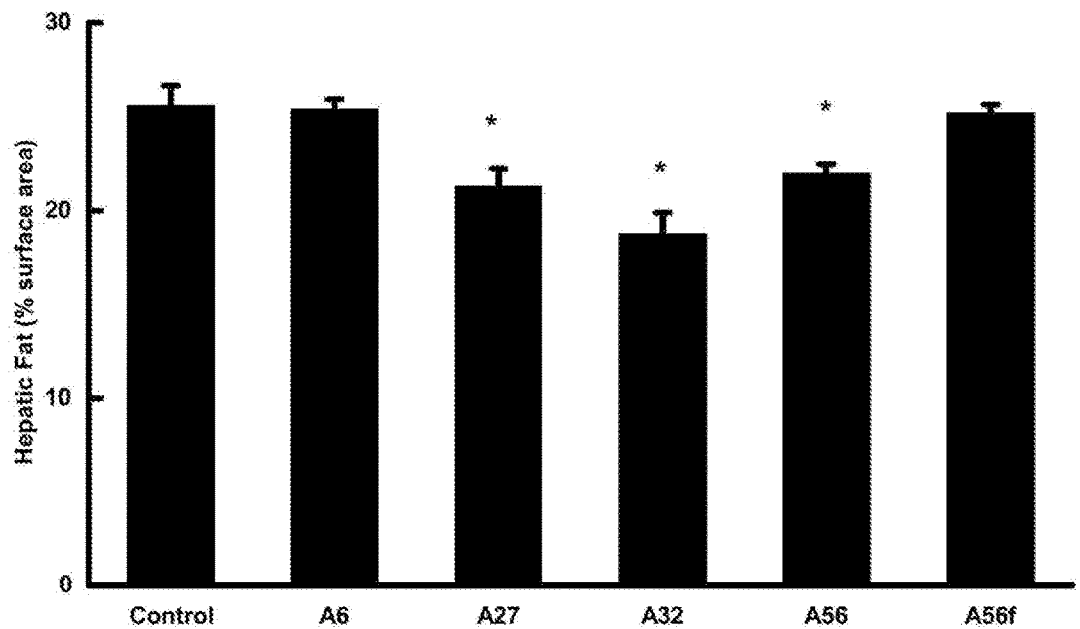
FIG. 20: Effect of test compounds on accumulation of fat in the liver in SHR on a high fat salt diet after 6 weeks treatment with compound in the drinking solution (10% ethanol) or drinking solution alone.

Fat in the liver after 4 weeks treatment with 500 pmol/kg/min of A27, A32 and A56 was reduced compared to 18 week controls (FIG. 20, *p<0.05) demonstrating that these compounds reduce accumulation of hepatic fat.

Figure 21:
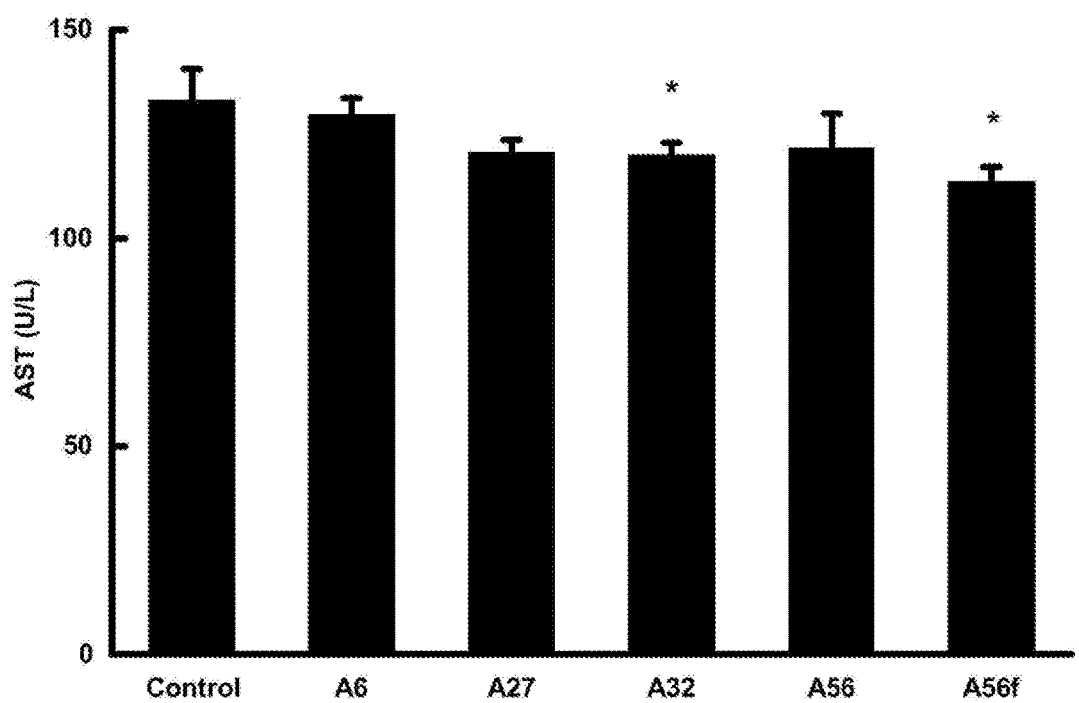
FIG. 21: Effect of treatment with test compound for 5 weeks on plasma aminotransferase (AST) levels in SHR on high fat diet and 10% ethanol drinking solution.

Plasma AST levels were decreased in rats treated with A32 and A56f compared to controls (FIG. 21, *p<0.025), demonstrating that these compounds prevent liver damage.

Example 15: Comparisons of In Vitro and In Vivo Screening of Compounds

Figure 22:
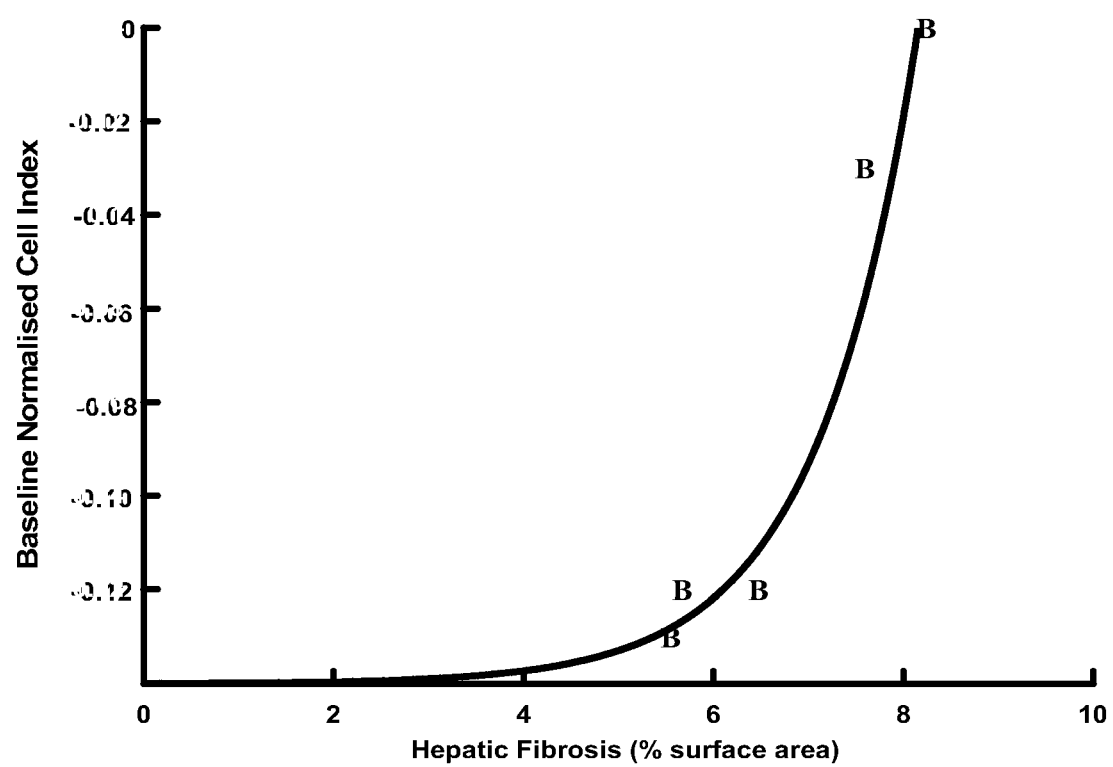
FIG. 22: Comparison of cell impedance in bovine aortic endothelial cells and the level of hepatic fibrosis in SHR on a high fat diet treated with test compounds.

A comparison of cell impedance in bovine aortic endothelial cells and the level of hepatic fibrosis in SHR treated with various test compounds showed that the in vitro assay is predictive of the ability of the test compounds to decrease fibrosis in the liver (FIG. 22, $R^2$=0.925).

The invention claimed is:
1. A compound of the formulae:

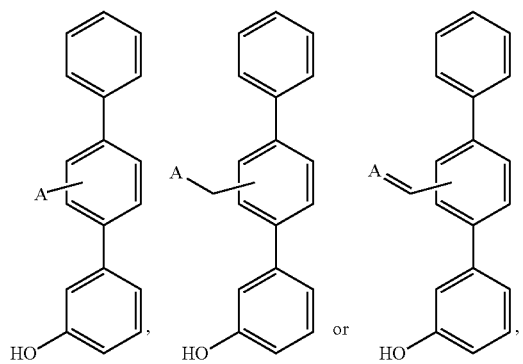

wherein:
A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl, or a pharmacologically acceptable salt, stereoisomer, diastereomer, enantiomer, racemate, hydrate and/or solvate thereof.

2. The compound according to claim 1, wherein the saturated, partly saturated or unsaturated 5- or 6-membered heterocyclyl contains one or more of N, S or O, optionally substituted with one or more oxo, $C_{1-6}$alkyl, amino, hydroxyl or halo substituents.

3. The compound according to claim 1, wherein the saturated, partly saturated or unsaturated 5- or 6-membered heterocyclyl is selected from pyrrolyl, pyrazolyl, imidazolyl, triazolyl, imidazolidinyl, pyrrolidinyl, pyrrolidinylidene, dihydropyrrolyl, isoxazolyl dihydrooxazolyl, isoxazolidinyl, oxazolidinyl and oxazolyl, optionally substituted with one or more oxo, $C_{1-6}$alkyl, amino, hydroxyl or halo substituents.

4. The compound according to claim 1, wherein the $C_{1-6}$alkoxyl amine is aminooxymethyl.

5. The compound according to claim 1, wherein the $C_{1-6}$alkyl amine is optionally substituted with one or more of $Cl_6$alkyl, $C_{1-6}$halo alkyl, hydroxyl or halo, preferably mono-, di- or tri-substituted halo alkyl, most preferably tri-fluoro methane.

6. The compound according to claim 1, wherein the $C_{0-6}$alkyl carboxylic acid is carboxylic acid.

7. The compound according to claim 1, wherein the $C_{1-6}$alkyl hydroxyl is methyl hydroxyl.

8. The compound according to claim 1, wherein the $C_{0-6}$alkyl bicyclic heterocyclyl is selected from indolyl, isoindolyl, insolinyl and isoindolinyl, optionally substituted with one or more oxo, preferably dioxo.

9. The compound according to claim 1, wherein the $C_{1-6}$alkoxyl bicyclic heterocyclyl is selected indolyl, isoindolyl, insolinyl and isoindolinyl, optionally substituted with one or more oxo, and wherein the $C_{1-6}$alkoxyl is methoxy or ethoxy.

10. The compound according to claim 1, wherein A is selected from:

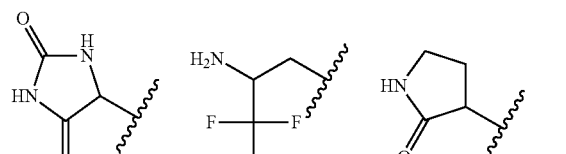

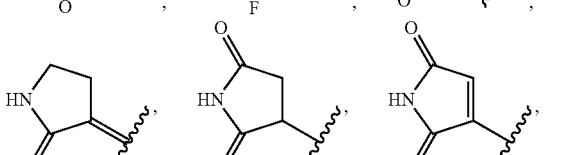

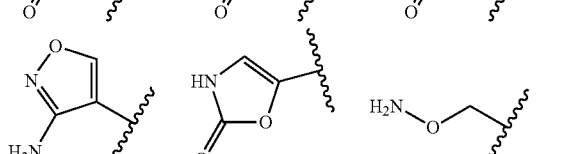

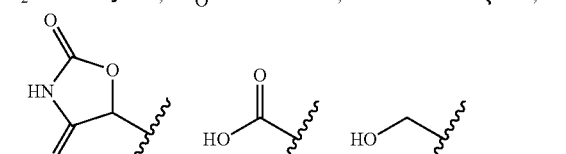

and

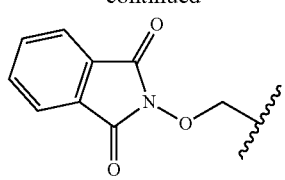

11. The compound according to claim 1, wherein the compound is selected from the group consisting of:

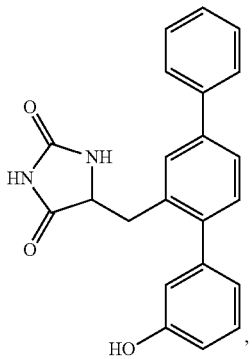

(A32)

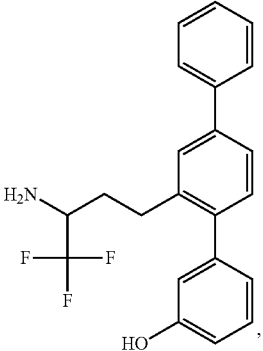

(A6)

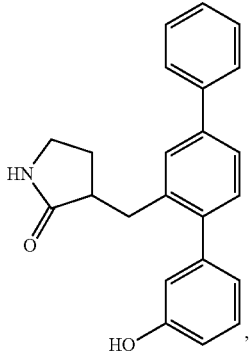

(A26)

-continued
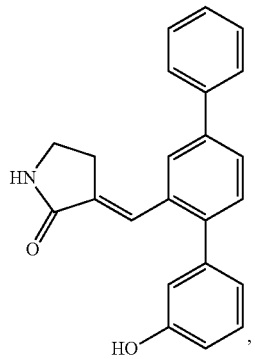
(A27)
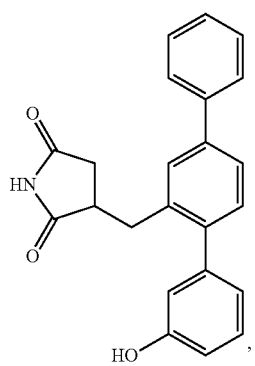
(A30)
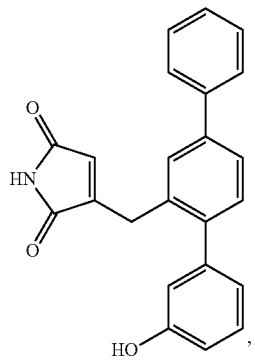
(A31)
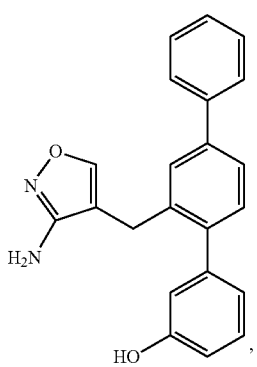
(A35)
-continued
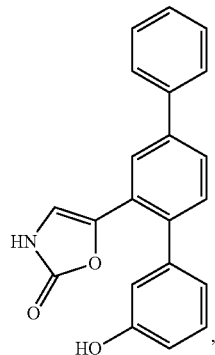
(A45)
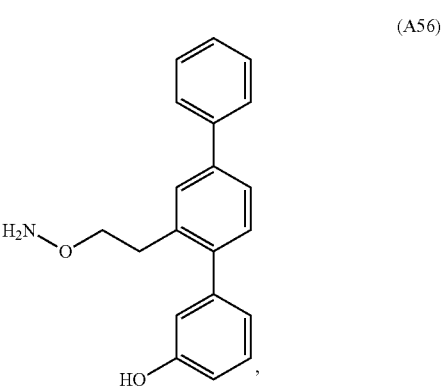
(A56)
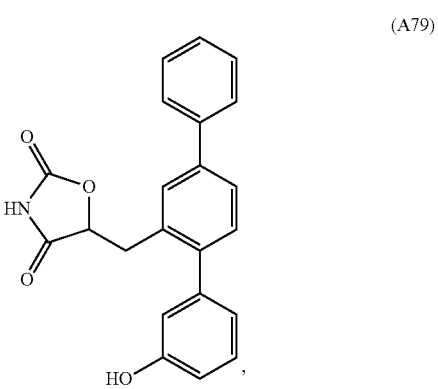
(A79)
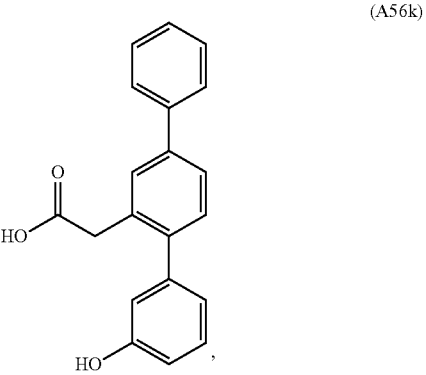
(A56k)

-continued (A56f)
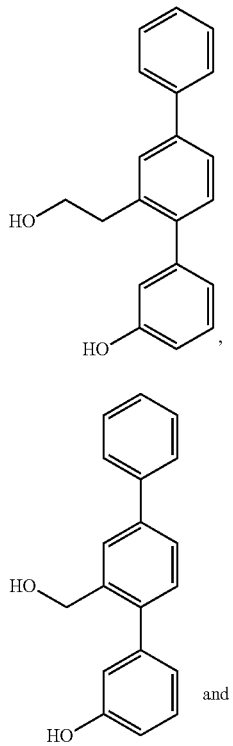

(A81)
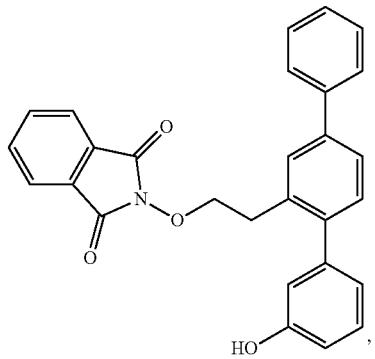 and (A56g)

or a pharmacologically acceptable salt, stereoisomer, diastereomer, enantiomer, racemate, hydrate and/or solvate thereof.

12. A pharmaceutical composition comprising a compound according to claim 1 and a pharmaceutically acceptable excipient.

13. A method for the prophylactic or therapeutic treatment of fibrosis in a subject comprising administering to the subject a compound according to claim 1.

14. The method according to claim 13, wherein the treatment prevents, reduces or slows the progression of fibrosis.

15. The method according to claim 13, wherein the treatment reduces established fibrosis.

16. The method according to claim 13, wherein the treatment restores normal tissue architecture.

17. The method according to claim 13, wherein the fibrosis is myocardial fibrosis, kidney fibrosis and/or liver fibrosis.

18. A method for preventing, reducing or slowing fat accumulation in the liver of a subject comprising administering to the subject a compound according to claim 1.

19. A method for preventing, reducing or slowing renal tubular cell death in a subject comprising administering to the subject a compound according to claim 1.

20. A method for restoring normal tissue architecture in a subject comprising administering to the subject a compound according to claim 1.

21. A compound of the formula:

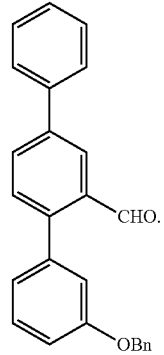 [SMILES: O=Cc1cc(-c2ccccc2)ccc1-c1cccc(OCc2ccccc2)c1]

* * * * *